US012780801B2

(12) United States Patent
Jones et al.

(10) Patent No.: US 12,780,801 B2

(45) Date of Patent: Nov. 3, 2026

(54) BINDERS OF CEREBLON AND METHODS OF USE THEREOF

(71) Applicant: DANA-FARBER CANCER INSTITUTE, INC., Boston, MA (US)

(72) Inventors: Lyn Howard Jones, Winchester, MA (US); Justin Cruite, Boston, MA (US)

(73) Assignee: DANA-FARBER CANCER INSTITUTE, INC., Boston, MA (US)

(*) Notice: Subject to any disclaimer, the term of this patent is extended or adjusted under 35 U.S.C. 154(b) by 294 days.

(21) Appl. No.: 18/695,529

(22) PCT Filed: Sep. 30, 2022

(86) PCT No.: PCT/US2022/077385

§ 371 (c)(1),
(2) Date: Mar. 26, 2024

(87) PCT Pub. No.: WO2023/056443

PCT Pub. Date: Apr. 6, 2023

(65) Prior Publication Data

US 2024/0409528 A1 Dec. 12, 2024

Related U.S. Application Data

(60) Provisional application No. 63/350,214, filed on Jun. 8, 2022, provisional application No. 63/251,344, filed on Oct. 1, 2021.

(51) Int. Cl.

| | |
|---|---|
| ***C07D 401/14*** | (2006.01) |
| ***A61K 31/454*** | (2006.01) |
| ***A61K 31/506*** | (2006.01) |
| ***C07D 401/04*** | (2006.01) |

(52) U.S. Cl.

CPC .......... *C07D 401/14* (2013.01); *A61K 31/454* (2013.01); *A61K 31/506* (2013.01); *C07D 401/04* (2013.01)

(58) Field of Classification Search

CPC ............................ C07D 401/14; C07D 401/04

See application file for complete search history.

(56) References Cited

U.S. PATENT DOCUMENTS

| | | | |
|---|---|---|---|
| 2015/0291562 | A1 | 10/2015 | Crew et al. |
| 2016/0243247 | A1 | 8/2016 | Bradner et al. |
| 2018/0215731 | A1 | 8/2018 | Crew et al. |

FOREIGN PATENT DOCUMENTS

| | | | |
|---|---|---|---|
| EP | 3778590 | A1 | 2/2021 |
| WO | 2013016441 | A1 | 1/2013 |
| WO | 2019196812 | A1 | 10/2019 |
| WO | 2020118098 | A1 | 6/2020 |
| WO | 2020173426 | A1 | 9/2020 |

OTHER PUBLICATIONS

Cruite et al. RSC Chem. Biol. 2022, 3, 1105-1110 (Year: 2022).*

CAS Registry Entry for Registry No. 2757894-69-0, which entered STN on Feb. 2, 2022 (Year: 2022).*

CAS Registry Entry for Registry No. 2803819-61-4, which entered STN on Aug. 11, 2022 (Year: 2022).*

CAS Registry Entry for Registry No. 2803819-63-6, which entered STN on Aug. 11, 2022 (Year: 2022).*

CAS Registry Entry for Registry No. 2803823-78-9, which entered STN on Aug. 11, 2022 (Year: 2022).*

Lin et al., "Development of Photolenalidomide for Cellular Target Identification," J. Am. Chem. Soc, 2022, vol. 144, pp. 606-614.

Enamine Store, Safety Data Sheet, "EN300-28318340 SDS", Feb. 6, 2015, 6 pages.

Pubchem CID 146081557, Create date: Jun. 5, 2020, 8 pages.

* cited by examiner

*Primary Examiner* — Matthew P Coughlin

(74) *Attorney, Agent, or Firm* — ArentFox Schiff LLP; Daniel W. Clarke; Shawn P. Foley

(57) ABSTRACT

The present application provides compounds that are binders of cereblon. Also disclosed are methods for the treatment of disorders modulated by WDYHV1, GSPT1, and PFKFB4.

32 Claims, 7 Drawing Sheets

Specification includes a Sequence Listing.

SEQUENCE LISTING

```
Sequence total quantity: 1
SEQ ID NO: 1          moltype = AA  length = 18
FEATURE               Location/Qualifiers
source                1..18
                      mol_type = protein
                      organism = Homo sapiens
MOD_RES               7
                      note = 347-364 histidine 353 covalently labeled
SEQUENCE: 1
AAYVNPHGYV HETLTVYK                                         18
```

BINDERS OF CEREBLON AND METHODS OF USE THEREOF

RELATED APPLICATIONS

This application is a national stage application, filed under 35 U.S.C. § 371, of International Application No. PCT/US2022/077385, filed Sep. 30, 2022, which claims the benefit of priority under 35 U.S.C. § 119(e) to U.S. Provisional Application No. 63/251,344, filed Oct. 1, 2021, and U.S. Provisional Application No. 63/350,214, filed Jun. 8, 2022, each of which is incorporated herein by reference in its entirety.

SEQUENCE LISTING

The instant application contains a Sequence Listing which has been submitted electronically in XML format and is hereby incorporated by reference in its entirety. Said XML copy, created on Sep. 7, 2022, is named 52095-732001WO_ST26.xml and is 2.25 KB bytes in size.

BACKGROUND

The gene that encodes cereblon (CRBN) was first identified in the course of a study of genes related to memory and learning. The gene was assigned the name CRBN based on its supposed role in the development of cerebral tissues and because its expression in the hippocampus among other areas, is associated with memory and learning processes. Higgins, et al., Neurol. 63(10):1927-31 (2004).

Cereblon is a 442-amino acid multifunctional protein located in the cytoplasm, nucleus and peripheral membrane of the human brain and other tissues (Wada et al., Biochem. & Biophys. Res. Comm. 477:388-94 (2016)). It interacts with the DNA damage-binding protein-1 (DDB1), Cullin 4 (Cul4A and Cul4B), and regulator of Cullins 1 (RoC1) to form the functional E3 ubiquitin ligase complex, which is known as the $CRL4^{CRBN}$ E3 ubiquitin ligase complex. Cereblon's role as part of this complex includes targeting proteins for proteolysis (also known as degradation) via a ubiquitin-proteasome pathway. See, e.g., Chang et al., Int. J. Biochem. Mol. Biol. 2(3):287-94 (2011).

Cereblon is closely associated with the metabolism and proliferation of normal cells as well as tumor cells. On one hand, its existence ensures normal metabolic function and normal physiological function of ion channels, which are important to maintaining cell growth and proliferation. On the other hand, cereblon is also involved in the etiology of many diseases, such as cancer. See, generally, Shi et al., J. Immunol. Res. Article ID 9130608 (2017).

Immunomodulatory drugs, or immunomodulatory imide drugs, ("IMiDs") area new class of anti-cancer drugs that include thalidomide and its analogs. Thalidomide has been approved by the FDA for treatment of multiple myeloma. In addition to thalidomide itself, two thalidomide analogs, lenalidomide and pomalidomide, have been approved by the FDA (and are being marketed under the names REVLIMID® and POMALYST®, respectively) for treatment of multiple myeloma (among other diseases). As suggested by their nomenclature, one of the first known properties of IMiDs was their immunomodulatory capacity, including cytokine modulation and T cell co-stimulation (Schafer et al., J. Pharmacol. & Exper. Ther. 305:1222-32 (2003)), resulting in interleukin-2 production in T cells. Subsequently, IMiDs were shown to have pleiotropic effects on a wide range of immune cells including natural killer (NK) cell activation and B cell and monocyte inhibition (Corral et al., J. Immunol. 163:380-6 (1999)).

Cereblon has been identified as a common primary target for IMiDs. For example, it has been reported that members of the Ikaros family of transcription factors, Ikaros and Aiolos (encoded by the genes Ikaros family zinc finger protein 1 (IKZF1) and IKZF3 respectively) are recruited as protein substrates for $CRL4^{CRBN}$ in T cells in response to treatment with lenalidomide and pomalidomide, resulting in enhanced production of IL-2 and other cytokines that regulate T cell function. See, Gandhi et al., Br. J. Hematol. 164:811-21 (2014). It has also been reported that lenalidomide, but not pomalidomide, induces the degradation of the protein kinase, casein kinase 1α (CK1α), which exploits CK1α haploinsufficiency associated with 5q-deletion associated myelodysplastic syndrome. See, Krönke et al., Nature 523:183-8 (2015). Structural studies have shown that these IMiDs bind in a shallow hydrophobic pocket on the surface of cereblon, and that the binding is mediated by the glutarimide ring that is common to thalidomide, lenalidomide and pomalidomide.

More recently, CRBN-binding compounds named "cereblon modulators" have been developed. For example, CC-122, a new chemical entity termed 'pleiotropic pathway modifier', binds cereblon and promotes degradation of Aiolos and Ikaros in diffuse large B-cell lymphoma (DLBCL) and T cells in vitro, in vivo, and in patients, resulting in both cell autonomous as well as immunostimulatory effects. See, Hagner et al., Blood 126(6):779-89 (2016). CC-885, another new cereblon modulator, has been reported to possess antitumor activity which is broader than that of thalidomide, lenalidomide and pomalidomide. CC-885 is mediated by cereblon-dependent ubiquitination and degradation of the translation termination factor glutathione S-transferase pi gene 1 (GSPT1). See, Matyskiela et al., Nature 535:252-7 (2016).

Cereblon modulators, also known as molecular glue compounds, induce protein-protein interactions that, in the context of a ubiquitin ligase, lead to protein degradation (Stanton et al., Science 359:eaao5902 (2018)). Unlike proteolysis-targeting chimeric molecules (PROTAC®s), molecular glue compounds are small molecules (also known as small molecule degraders) that induce an interaction between a substrate receptor of an E3 ubiquitin ligase and a target protein leading to proteolysis of the target. Examples of molecular glues that induce proteolysis of targets include IMiDs (immune modulatory drugs; e.g., thalidomide), which generate a novel interaction between a substrate (e.g., IKZF1/3) and cereblon, a substrate receptor (also known as DCAF) for Cullin-RING ubiquitin ligase 4 (CRL4) den Besten and Lipford, Nat. Chem. Biol. 16(11):1157-1158 (2020). Unlike traditional enzyme inhibitors, these molecular glue degraders act substoichiometrically to catalyze the rapid depletion of previously inaccessible targets (Chopra et al., Drug Discov. Today. Technol. 31:5-13 (2019)). Although highly desirable, molecular glue degraders have only been found serendipitously. Strategies available for identifying or designing these compounds are limited (Slabicki et al., Nature DOI: 10.1038/s41586-020-2374-x (2020)).

The exploitation of cereblon as a mediator in disease treatment has also led to the development of hetero-bifunctional PROTAC®s (PROteolysis TArgeting Chimera) that recruit targeted proteins that are themselves disease mediators (e.g., bromodomain-containing protein 4 (BRD4)) to $CRL4^{CRBN}$ E3 ubiquitin ligase, leading to degradation of the targeted protein. See, e.g., Lu et al., Cell Cancer Biol. 22(6):755-63 (2015).

SUMMARY

A first aspect of the present disclosure is directed to a compound of formula (I)

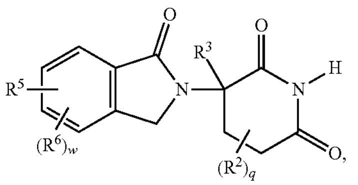

(I)

or a pharmaceutically acceptable salt or stereoisomer thereof, wherein each $R^2$ is independently $C_1$-$C_3$ alkyl, $R^3$ is H or $C_1$-$C_3$ alkyl, $R^5$ is —$SO_2F$, —$OSO_2F$, —$SO_2$—CH═$CH_2$, —$NHSO_2$—CH═$CH_2$, —$SO_2$-(optionally substituted triazolyl), —$SO_2$-(optionally substituted pyrazolyl), —$SO_2$-(optionally substituted imidazolyl), or —$SO_2$-(optionally substituted pyrimidindionyl), each $R^6$ is independently halogen, —OH, —$N(R')_2$, $C_1$-$C_6$ alkyl, or $C_1$-$C_6$ alkoxy, each R' is independently H or $C_1$-$C_6$ alkyl, q is 0, 1, or 2, and w is 0, 1, 2, or 3.

Another aspect of the present disclosure is directed to a method of making the compounds of formula (I) and their pharmaceutically acceptable salts and stereoisomers.

Another aspect of the disclosure is directed to a pharmaceutical composition, comprising a therapeutically effective amount of a compound of formula (I) or pharmaceutically acceptable salt or stereoisomer thereof, and a pharmaceutically acceptable carrier. In some embodiments, the pharmaceutical composition is in the form of a solid. In some embodiments, the pharmaceutical composition is in the form of a tablet or capsule. In some embodiments, the pharmaceutical composition is in the form of a liquid.

Another aspect of the disclosure is directed to a method of treating a disease or disorder that is characterized by aberrant activity of Protein N-terminal glutamine amidohydrolase (NTAQ1 or WDYHV1), G1 to S phase transition protein 1 (GSPT1), or 6-phosphofructo-2-kinase/fructose-2, 6-biphosphatase 4 (PFKFB4), comprising administering to a subject in need thereof a therapeutically effective amount of a compound of formula (I) or a pharmaceutically acceptable salt or stereoisomer thereof.

Another aspect of the disclosure is directed to a method of reducing the level of WDYHV1, GSPT1, or PFKFB4 in a cell, either in vitro or in vivo, comprising contacting the cell with an effective amount of a compound of formula (I) or pharmaceutically acceptable salt or stereoisomer thereof.

Another aspect of the disclosure is directed to a method of covalently engaging cereblon, comprising contacting cereblon with a compound of formula (I), or a stereoisomer or pharmaceutically acceptable salt thereof, wherein the compound binds or labels Histidine353 of cereblon.

Another aspect of the disclosure is directed to a method of blocking an immunomodulatory drug binding pocket of cereblon, comprising contacting cereblon with a compound of formula (I), or a stereoisomer or pharmaceutically acceptable salt thereof, wherein binding of the compound with cereblon inhibits binding between cereblon and any entity that causes cereblon-mediated degradation of a protein target.

Cysteine targeting covalent chemical probes were used previously to identify ligandable E3 ligases, leading to the development of covalent PROTAC®s that recruit RNF114 and DCAF16 E3 ligases (See Spradlin et al., Nat Chem Biol 15(7):747-55 (2019); Zhang et al., Nat Chem Biol 15(7): 737-46 (2019)). However, previously reported covalent modulators of cereblon inhibited degrader action. U.S. Patent Application Publication 2020/0216507 A1, to Weinstein, et al. describes a compound that covalently labels cysteine residue C287 and inhibits an FKBP12 PROTAC®. Many functional binding sites do not possess a reactive cysteine residue that would traditionally be used to develop covalent small molecule modulators, including the ligand binding site of cereblon responsible for recruiting degraded targets. For example, there are no available cysteine residues in the immunomodulatory drug binding site of cereblon by which to develop a covalent degrader. The present compounds are believed to engage Histidine353 in cereblon.

BRIEF DESCRIPTION OF THE DRAWINGS

FIG. 3A shows mass spectra (left) and zero-charge mass spectra (right) of the CRBN-DDB1 complex treated with DMSO (top) or an equimolar concentration of compound 1 for 24 hours at room temperature (bottom). FIG. 3B is a MS/MS spectrum of CRBN peptide modified with compound 1 indicating covalent labeling of His353.

DETAILED DESCRIPTION

Figure 1:
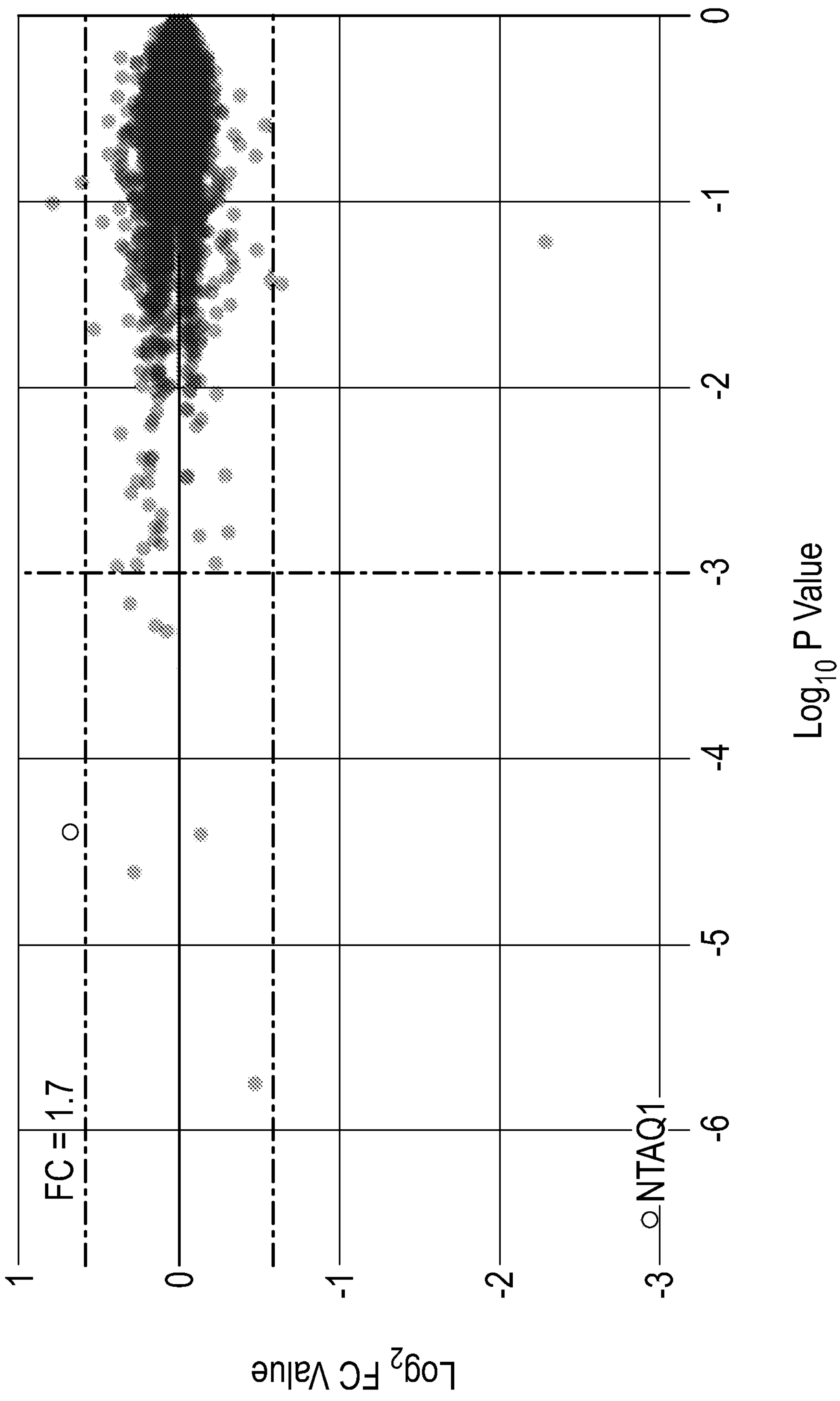
FIG. 1 is a graph of $Log_2$ fold-change (FC) value versus $Log_{10}$ P value for compound 1 for various potential protein targets showing that compound 1 downregulates Protein N-terminal glutamine amidohydrolase (NTAQ1 or WDYHV1).

Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the present disclosure.

As used in the description and the appended claims, the singular forms “a”, “an”, and “the” include plural referents unless the context clearly dictates otherwise. Thus, for example, reference to “a composition” includes mixtures of two or more such compositions, reference to “an inhibitor” includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed disclosure.

With respect to compounds of the present disclosure, and to the extent the following terms are used herein to further describe them, the following definitions apply.

As used herein, and to the extent not used in the context of any specific group or moiety, the term "alkyl" refers to a saturated linear or branched-chain monovalent hydrocarbon radical. In one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_8$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group.

As used herein, and to the extent not used in the context of any specific group or moiety, the term "alkenyl" refers to a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is a $C_2$-$C_{18}$ group. In other embodiments, the alkenyl radical is a $C_2$-$C_{12}$, $C_2$-$C_{10}$, $C_2$-$C_8$, $C_2$-$C_6$ or $C_2$-$C_3$ group. Examples include ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

As used herein, and to the extent not used in the context of any specific group or moiety, the terms "alkoxyl" or "alkoxy" refer to an alkyl group, as defined above, having an oxygen radical attached thereto, which is the point of attachment. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl.

As used herein, the term "halogen" (or "halo" or "halide") refers to fluorine, chlorine, bromine and iodine.

As used herein, the term "cyclic group" broadly refers to any group that used alone or as part of a larger moiety, contains a saturated, partially saturated or aromatic ring system e.g., carbocyclic (cycloalkyl, cycloalkenyl), heterocyclic (heterocycloalkyl, heterocycloalkenyl), aryl and heteroaryl groups. Cyclic groups may have one or more (e.g., fused) ring systems. Thus, for example, a cyclic group can contain one or more carbocyclic, heterocyclic, aryl or heteroaryl groups.

As used herein, the term "carbocyclic" (also "carbocyclyl") refers to a group that used alone or as part of a larger moiety, contains a saturated, partially unsaturated, or aromatic ring system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_8$, $C_3$-$C_6$ or $C_5$-$C_6$. In some embodiments, carbocyclyl, as a bicycle, includes $C_7$-$C_{12}$. In another embodiment, carbocyclyl, as a spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocyclyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

Thus, the term carbocyclic also embraces carbocyclylalkyl groups which as used herein refer to a group of the formula —$R^c$-carbocyclyl where $R^c$ is an alkyl group. The term carbocyclic also embraces carbocyclylalkoxy groups which as used herein refer to a group bonded through an oxygen atom of the formula —O—$R^c$-carbocyclyl where $R^c$ is an alkyl group.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or $S(O)_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and spiro ring systems, wherein the ring atoms are carbon, and one to 5 ring atoms is a heteroatom such as nitrogen, sulfur, or oxygen. In some embodiments, heterocyclyl includes 3- to 7-membered monocycles having one or more heteroatoms selected from nitrogen, sulfur, or oxygen. In some embodiments, heterocyclyl includes 4- to 6-membered monocycles having one or more heteroatoms selected from nitrogen, sulfur, or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, thiophenyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Thus, the term "heterocyclic" embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$-heterocyclyl where $R^c$ is an alkyl group. The term heterocyclic also embraces heterocyclylalkoxy groups which as used herein refer to a radical bonded through an oxygen atom of the formula —O—$R^c$-heterocyclyl where $R^c$ is an alkyl group.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, naphthyridinyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring. The structure of any aryl group that is capable of having double bonds positioned differently is considered so as to embrace any and all such resonance structures.

Thus, the term aryl embraces aralkyl groups (e.g., benzyl) which as disclosed above refer to a group of the formula —$R^c$-aryl where $R^c$ is an alkyl group such as methylene or ethylene. In some embodiments, the aralkyl group is an optionally substituted benzyl group. The term aryl also embraces aralkoxy groups which as used herein refer to a group bonded through an oxygen atom of the formula —O—$R^c$-aryl where $R^c$ is an alkyl group such as methylene or ethylene.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 5-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, imidazopyridyl, pyrazinyl, pyridazinyl, triazinyl, tetrazinyl, tetrazolo[1,5-b]pyridazinyl, purinyl, deazapurinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, indolizinyl, isoindolyl, benzothienyl, benzothiophenyl, methylenedioxyphenyl, benzofuranyl, dibenzofuranyl, indazolyl, benzimidazolyl, benzodioxazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tri-cyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring. The structure of any heteroaryl group that is capable of having double bonds positioned differently is considered so as to embrace any and all such resonance structures.

The term heteroaryl also embraces N-heteroaryl groups which as used herein refers to a heteroaryl group, as defined above, and which contains at least one nitrogen atom and where the point of attachment of the N-heteroaryl group to the rest of the molecule is through a nitrogen atom in the heteroaryl group. The term heteroaryl further embraces C-heteroaryl groups which as used herein refer to a heteroaryl group as defined above and where the point of attachment of the heteroaryl group to the rest of the molecule is through a carbon atom in the heteroaryl group. The term heteroaryl further embraces heteroarylalkyl groups which as disclosed above refer to a group of the formula —$R^c$-heteroaryl, wherein $R^c$ is an alkyl group as defined above. The term heteroaryl further embraces heteroaralkoxy (or heteroarylalkoxy) groups which as used herein refer to a group bonded through an oxygen atom of the formula —O—$R^c$-heteroaryl, where $R^c$ is an alkyl group as defined above.

Unless disclosed to the contrary, any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1, 2, 3, or 4) heteroatoms such as oxygen, sulfur, and nitrogen grouped in a linear, branched, or cyclic structural format.

To the extent not disclosed otherwise for any particular group(s), representative examples of substituents may thus include alkyl, substituted alkyl (e.g., $C_1$-$C_6$, $C_{1-5}$, $C_{1-4}$, $C_{1-3}$, $C_{1-2}$, $C_1$), alkoxy (e.g., $C_1$-$C_6$, $C_{1-5}$, $C_{1-4}$, $C_{1-3}$, $C_{1-2}$, $C_1$), substituted alkoxy (e.g., $C_1$-$C_6$, $C_{1-5}$, $C_{1-4}$, $C_{1-3}$, $C_{1-2}$, $C_1$), haloalkyl (e.g., $CF_3$), alkenyl (e.g., $C_2$-$C_6$, $C_{2-5}$, $C_{2-4}$, $C_{2-3}$, $C_2$), substituted alkenyl (e.g., $C_2$-$C_6$, $C_{2-5}$, $C_{2-4}$, $C_{2-3}$, $C_2$), alkynyl (e.g., $C_2$-$C_6$, $C_{2-5}$, $C_{2-4}$, $C_{2-3}$, $C_2$), substituted alkynyl (e.g., $C_2$-$C_6$, $C_{2-5}$, $C_{2-4}$, $C_{2-3}$, $C_2$), cyclic (e.g., $C_3$-$C_{12}$, $C_5$-$C_6$), substituted cyclic (e.g., $C_3$-$C_{12}$, $C_5$-$C_6$), carbocyclic (e.g., $C_3$-$C_{12}$, $C_5$-$C_6$), substituted carbocyclic (e.g., $C_3$-$C_{12}$, $C_5$-$C_6$), heterocyclic (e.g., $C_3$-$C_{12}$, $C_5$-$C_6$), substituted heterocyclic (e.g., $C_3$-$C_{12}$, $C_5$-$C_6$), aryl (e.g., benzyl and phenyl), substituted aryl (e.g., substituted benzyl or phenyl), heteroaryl (e.g., pyridyl or pyrimidyl), substituted heteroaryl (e.g., substituted pyridyl or pyrimidyl), aralkyl (e.g., benzyl), substituted aralkyl (e.g., substituted benzyl), halo, hydroxyl, aryloxy (e.g., $C_6$-$C_{12}$, $C_6$), substituted aryloxy (e.g., $C_6$-$C_{12}$, $C_6$), alkylthio (e.g., $C_1$-$C_6$), substituted alkylthio (e.g., $C_1$-$C_6$), arylthio (e.g., $C_6$-$C_{12}$, $C_6$), substituted arylthio (e.g., $C_6$-$C_{12}$, $C_6$), cyano, carbonyl, substituted carbonyl, carboxyl, substituted carboxyl, amino, substituted amino, amido, substituted amido, thio, substituted thio, sulfinyl, substituted sulfinyl, sulfonyl, substituted sulfonyl, sulfinamide, substituted sulfinamide, sulfonamide, substituted sulfonamide, urea, substituted urea, carbamate, substituted carbamate, amino acid, and peptide groups.

The term "binding" as it relates to interaction between the compound of formula (I) and cereblon refers to an interaction that may be covalent or non-covalent, and reversible or irreversible. In some embodiments, the compounds of formula (I) act as molecular glue in the sense that they recruit cereblon to the target protein, to function as a catalyst for targeted protein degradation.

The term "binding" as it relates to interaction between the $R^5$ group attached to the phenyl ring in the compound of formula (I) and cereblon, typically refers to a covalent interaction, which may be reversible or irreversible. In some embodiments, the interaction between the $R^5$ group attached to the phenyl ring in the compound of formula (I) and cereblon, is a non-covalent interaction.

A first aspect of the present disclosure is directed to a compound of formula (I)

(I)

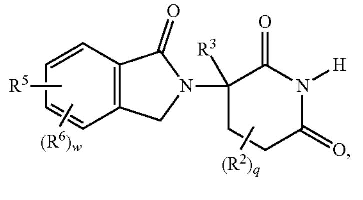

or a pharmaceutically acceptable salt or stereoisomer thereof, wherein each $R^2$ is independently $C_1$-$C_3$ alkyl, $R^3$ is H or $C_1$-$C_3$ alkyl, $R^5$ is —$SO_2F$, —$OSO_2F$, —$SO_2$—CH=$CH_2$, —$NHSO_2$—CH=$CH_2$, —$SO_2$-(optionally substituted triazolyl), —$SO_2$-(optionally substituted pyrazolyl), —$SO_2$-(optionally substituted imidazolyl), or —$SO_2$-(optionally substituted pyrimidindionyl), each $R^6$ is independently halogen, —OH, —$N(R')_2$, $C_1$-$C_6$ alkyl, or $C_1$-$C_6$ alkoxy, each R' is independently H or $C_1$-$C_6$ alkyl, q is 0, 1, or 2, and w is 0, 1, 2, or 3.

In some embodiments, $R^3$ is H.

In some embodiments, $R^5$ is —$SO_2F$. In some embodiments, $R^5$ is —$OSO_2F$. In some embodiments, $R^5$ is —$SO_2$—CH═$CH_2$. In some embodiments, $R^5$ is —$NHSO_2$—CH═$CH_2$. In some embodiments, $R^5$ is —$SO_2$-(optionally substituted triazolyl). In some embodiments, the optionally substituted triazolyl is 1,2,3-triazol-2-yl, 1,2,3-triazol-1-yl, or 1,2,4-triazol-1-yl. In some embodiments, the triazole is substituted with $C_1$-$C_6$ alkyl, $C_1$-$C_6$ alkoxy, halo (e.g., F, Cl), CN, or haloalkyl (e.g., $CF_3$, $CHF_2$, $CH_2F$). In some embodiments, $R^5$ is —$SO_2$-(2H-1,2,3-triazol-2-yl). In some embodiments, $R^5$ is —$SO_2$-(1H-1,2,4-triazol-1-yl). In some embodiments, $R^5$ is —$SO_2$-(optionally substituted pyrazolyl). In some embodiments, $R^5$ is 1,2-pyrazol-1-yl. In some embodiments, the pyrazole is substituted with $C_1$-$C_6$ alkyl, $C_1$-$C_6$ alkoxy, halo (e.g., F, Cl), CN, or haloalkyl (e.g., $CF_3$, $CHF_2$, $CH_2F$). In some embodiments, $R^5$ is —$SO_2$-(4-methyl-1H-pyrazol-1-yl). In some embodiments, $R^5$ is —$SO_2$-(4-fluoro-1H-pyrazol-1-yl). In some embodiments, $R^5$ is —$SO_2$-(4-(trifluoromethyl)-1H-pyrazol-1-yl). In some embodiments, $R^5$ is —$SO_2$-(3-(trifluoromethyl)-1H-pyrazol-1-yl). In some embodiments, $R^5$ is —$SO_2$-(3-fluoro-1H-pyrazol-1-yl). In some embodiments, $R^5$ is —$SO_2$-(optionally substituted imidazolyl). In some embodiments, $R^5$ is 1,2-imidazol-1-yl, or 1,3-imidazol-1-yl. In some embodiments, the imidazole is substituted with $C_1$-$C_6$ alkyl, $C_1$-$C_6$ alkoxy, halo (e.g., F, Cl), CN, or haloalkyl (e.g., $CF_3$, $CHF_2$, $CH_2F$). In some embodiments, $R^5$ is —$SO_2$-(4-(trifluoromethyl)-1H-imidazol-1-yl). In some embodiments, $R^5$ is —$SO_2$-(4-methyl-1H-imidazol-1-yl). In some embodiments, $R^5$ is —$SO_2$-(4-fluoro-1H-imidazol-1-yl). In some embodiments, $R^5$ is —$SO_2$-(optionally substituted pyrimidindionyl). In some embodiments, $R^5$ is pyrimidin-2,4-dionyl. In some embodiments, the pyrimidinedione is substituted with $C_1$-$C_6$ alkyl, $C_1$-$C_6$ alkoxy, halo (e.g., F, Cl), $NH_2$, CN, or haloalkyl (e.g., $CF_3$, $CHF_2$, $CH_2F$). In some embodiments, $R^5$ is —$SO_2$-(5-methylpyrimidine-2,4(1H,3H)-dione). In some embodiments, $R^5$ is —$SO_2$-(5-aminopyrimidine-2,4(1H,3H)-dione). In some embodiments, $R^5$ is —$SO_2$-(pyrimidine-2,4(1H,3H)-dione).

In some embodiments, $R^6$ is —$CH_3$.

In some embodiments, $R^6$ is —$NH_2$.

In some embodiments, q is 0.

In some embodiments, w is 0. In some embodiments, w is 1.

In some embodiments, q is 0 and $R^3$ is H.

In some embodiments, q is 0, w is 0, and $R^3$ is H.

In some embodiments, q is 0, w is 0, $R^3$ is H, and $R^5$ is —$SO_2F$.

In some embodiments, q is 0, w is 0, $R^3$ is H, and $R^5$ is —$OSO_2F$.

In some embodiments, q is 0, w is 0, $R^3$ is H, and $R^5$ is —$SO_2$-(2H-1,2,3-triazol-2-yl).

In some embodiments, q is 0, w is 0, $R^3$ is H, and $R^5$ is —$SO_2$-(1H-1,2,4-triazol-1-yl).

In some embodiments, q is 0, w is 0, $R^3$ is H, and $R^5$ is —$SO_2$—CH═$CH_2$.

In some embodiments, q is 0, w is 0, $R^3$ is H, and $R^5$ is —$NHSO_2$—CH═$CH_2$.

In some embodiments, q is 0, w is 0, $R^3$ is H, and $R^5$ is —$SO_2$-(4-methyl-1H-pyrazol-1-yl).

In some embodiments, q is 0, w is 0, $R^3$ is H, and $R^5$ is —$SO_2$-(4-fluoro-1H-pyrazol-1-yl).

In some embodiments, q is 0, w is 0, $R^3$ is H, and $R^5$ is —$SO_2$-(4-(trifluoromethyl)-1H-pyrazol-1-yl).

In some embodiments, q is 0, w is 0, $R^3$ is H, and $R^5$ is —$SO_2$-(3-(trifluoromethyl)-1H-pyrazol-1-yl).

In some embodiments, q is 0, w is 0, $R^3$ is H, and $R^5$ is —$SO_2$-(3-fluoro-1H-pyrazol-1-yl).

In some embodiments, q is 0, w is 0, $R^3$ is H, and $R^5$ is —$SO_2$-(4-(trifluoromethyl)-1H-imidazol-1-yl).

In some embodiments, q is 0, w is 0, $R^3$ is H, and $R^5$ is —$SO_2$-(4-methyl-1H-imidazol-1-yl).

In some embodiments, q is 0, w is 0, $R^3$ is H, and $R^5$ is —$SO_2$-(4-fluoro-1H-imidazol-1-yl).

In some embodiments, q is 0, w is 0, $R^3$ is H, and $R^5$ is —$SO_2$-(5-methylpyrimidine-2,4(1H,3H)-dione).

In some embodiments, q is 0, w is 0, $R^3$ is H, and $R^5$ is —$SO_2$-(5-aminopyrimidine-2,4(1H,3H)-dione).

In some embodiments, q is 0, w is 0, $R^3$ is H, and $R^5$ is —$SO_2$-(pyrimidine-2,4(1H,3H)-dione).

In some embodiments, q is 0, w is 1, $R^3$ is H, $R^5$ is —$OSO_2F$, and $R^5$ is —$NH_2$.

In some embodiments, the compound or a pharmaceutically acceptable salt or stereoisomer thereof is

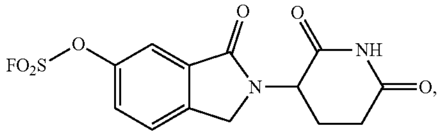

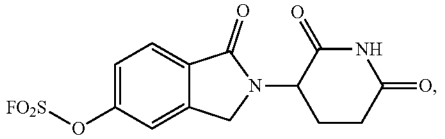

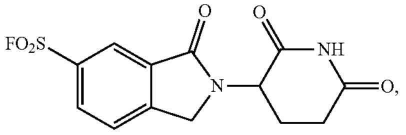

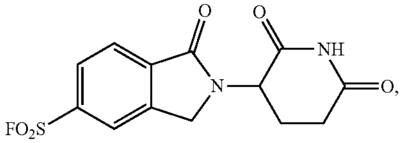

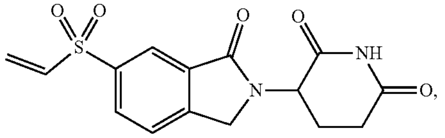

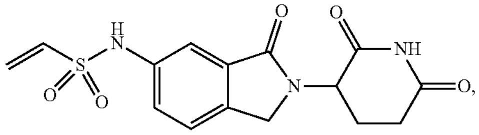

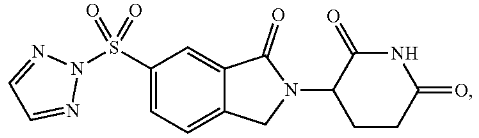

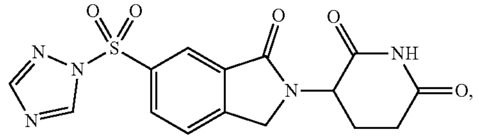

-continued

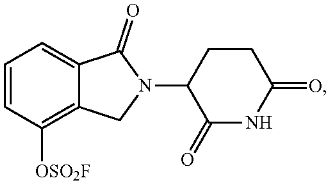

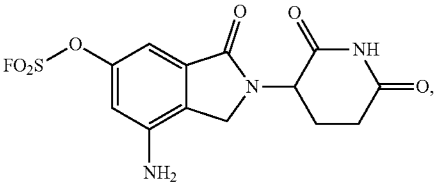

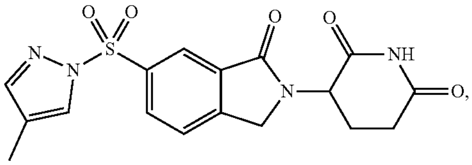

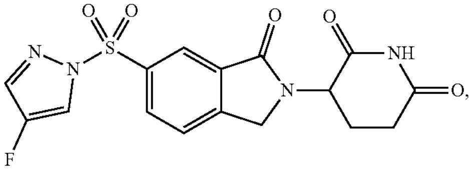

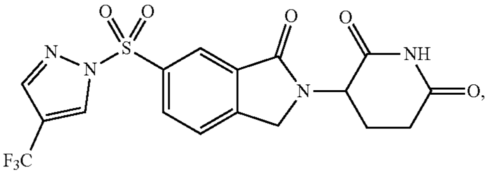

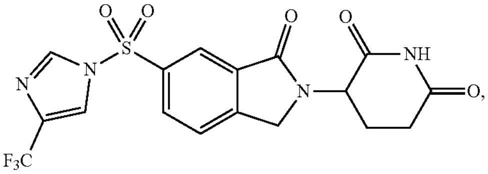

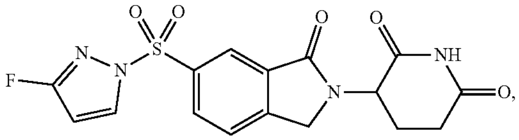

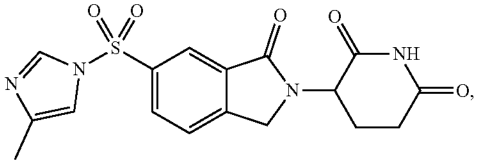

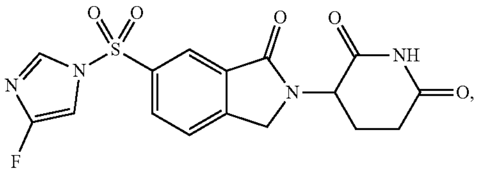

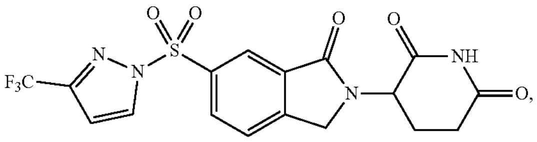

-continued

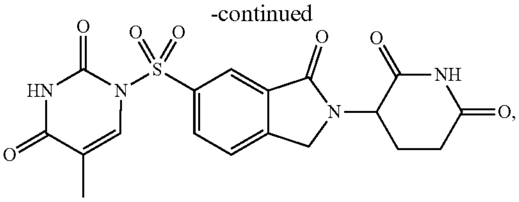

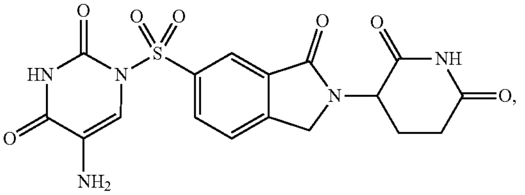

or

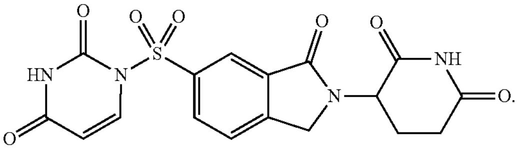

Structural studies have shown that immunomodulatory drugs (e.g., thalidomide, lenalidomide, pomalidomide, etc.) bind in a shallow hydrophobic pocket on the surface of cereblon, also referred to as the "tri-Trp" pocket, formed by three conserved surface tryptophan residues in the immunomodulatory drug binding domain (Morn et al., Scientific Reports, 8:1294 (2018)). Binding is mediated by the glutarimide ring that is common to thalidomide, lenalidomide and pomalidomide.

In some embodiments is provided a method of blocking an immunomodulatory drug (e.g., thalidomide, lenalidomide, pomalidomide) binding pocket of cereblon, comprising contacting cereblon with the compound of formula (I), or stereoisomer or pharmaceutically acceptable salt thereof, wherein binding of the compound with cereblon inhibits binding between cereblon and any entity that causes cereblon-mediated degradation of a protein target.

In some embodiments is provided a method of covalently engaging cereblon, comprising contacting cereblon with the compound of formula (I), or stereoisomer or pharmaceutically acceptable salt thereof, wherein the compound binds or labels Histidine353 of cereblon.

Compounds of formula (I) may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the compound of the present disclosure with a suitable acid or a base. Examples of pharmaceutically acceptable salts of the compounds of this disclosure include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the disclosure can form pharmaceutically acceptable salts with various organic bases such as lysine, arginine, guanidine, diethanolamine or metformin.

Compounds of formula (I) may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R-) or (S-) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R—) form is considered equivalent to administration of the compound in its (S—) form. Accordingly, the compounds of the present disclosure may be made and used in the form of individual isomers and substantially free of other isomers, or in the form of a mixture of various isomers, e.g., racemic mixtures of stereoisomers.

In some embodiments, the compound of formula (I) is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e., $^2H$, may afford certain therapeutic advantages resulting from greater metabolic stability, for example, increased in vivo half-life or reduced dosage requirements, and thus may be advantageous in some circumstances.

In addition, compounds of formula (I) embrace the use of N-oxides, crystalline forms (also known as polymorphs), active metabolites of the compounds having the same type of activity, tautomers, and unsolvated as well as solvated forms with pharmaceutically acceptable solvents such as water, ethanol, and the like, of the compounds. The solvated forms of the conjugates presented herein are also considered to be disclosed herein.

Methods of Synthesis

In some embodiments, the present disclosure is directed to a method for making a compound of formula (I) or a pharmaceutically acceptable salt or stereoisomer thereof. Broadly, the compounds of formula (I) or pharmaceutically acceptable salts or stereoisomers thereof, may be prepared by any process known to be applicable to the preparation of chemically related compounds. The compounds of the present disclosure will be better understood in connection with the synthetic schemes that described in various working examples and which illustrate nonlimiting methods by which the compounds of the disclosure may be prepared.

Pharmaceutical Compositions

Another aspect of the present disclosure is directed to a pharmaceutical composition that includes a therapeutically effective amount of a compound of formula (I) or a pharmaceutically acceptable salt or stereoisomer thereof, and a pharmaceutically acceptable carrier. The term "pharmaceutically acceptable carrier," as known in the art, refers to a pharmaceutically acceptable material, composition, or vehicle, suitable for administering compounds of the present disclosure to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may include one or more pharmaceutically acceptable excipients.

Broadly, compounds of formula (I) and their pharmaceutically acceptable salts and stereoisomers may be formulated into a given type of composition in accordance with conventional pharmaceutical practice such as conventional mixing, dissolving, granulating, dragee-making, levigating, emulsifying, encapsulating, entrapping and compression processes (see, e.g., *Remington: The Science and Practice of Pharmacy* (20th ed.), ed. A. R. Gennaro, Lippincott Williams & Wilkins, 2000 and *Encyclopedia of Pharmaceutical Technology*, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, the compounds are formulated for oral or intravenous administration (e.g., systemic intravenous injection).

Accordingly, compounds of the present disclosure may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams), and gases (e.g., propellants for aerosol compositions). Compounds may also be formulated for rapid, intermediate, or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, compounds of the present disclosure may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups, and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include excipients such as wetting agents, suspending agents, coloring, sweetening, flavoring, and perfuming agents.

Injectable preparations may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, compounds of formula (I) may be administered in a local rather than systemic manner, for example, via injection of the conjugate directly into an organ, often in a depot preparation or sustained release formulation. In specific embodiments, long-acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The compounds may be formulated for buccal or sublingual administration, examples of which include tablets, lozenges, and gels.

The compounds may be formulated for administration by inhalation. Various forms suitable for administration by inhalation include aerosols, mists, or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Compounds of formula (I) may be formulated for topical administration which as used herein, refers to administration intradermally by application of the formulation to the epidermis. These types of compositions are typically in the form of ointments, pastes, creams, lotions, gels, solutions, or sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation*

*Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerin, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a compound of formula (I) or a pharmaceutically acceptable salt or a stereoisomer thereof, effective in producing the desired therapeutic response in a particular patient suffering from a disease or disorder characterized or mediated by (e.g., involving) aberrant activity of WDYHV1, GSPT1, or PFKFB4. The term "therapeutically effective amount" thus includes the amount of a compound of the disclosure or a pharmaceutically acceptable salt or a stereoisomer thereof, that when administered, induces a positive modification in the disease or disorder to be treated, or is sufficient to prevent development or progression of the disease or disorder, or alleviate to some extent, one or more of the symptoms of the disease or disorder being treated in a subject, or which simply kills or inhibits the growth of diseased (e.g., neuroblastoma) cells, or reduces the amount of WDYHV1, GSPT1, or PFKFB4 in diseased cells.

The total daily dosage of the compounds and usage thereof may be decided in accordance with standard medical practice, e.g., by the attending physician using sound medical judgment. The specific therapeutically effective dose for any particular subject may depend upon a variety of factors, including: the disease or disorder being treated and the severity thereof (e.g., its present status); the age, body weight, general health, sex and diet of the subject; the time of administration, route of administration, and rate of excretion of the specific compound employed; the duration of the treatment; drugs used in combination or coincidental with the compound; and like factors well known in the medical arts (see, for example, *Goodman and Gilman's, The Pharmacological Basis of Therapeutics,* 10th Edition, A. Gilman, J. Hardman and L. Limbird, eds., McGraw-Hill Press, 155-173, 2001).

Compounds of formula (I) and their pharmaceutically acceptable salts and stereoisomers may be effective over a wide dosage range. In some embodiments, the total daily dosage (e.g., for adult humans) may range from about 0.001 to about 1600 mg, from 0.01 to about 1600 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, and in yet other embodiments from about 10 to about 30 mg per day. Individual dosages may be formulated to contain the desired dosage amount depending upon the number of times the compound is administered per day. By way of example, capsules may be formulated with from about 1 to about 200 mg of a compound (e.g., 1, 2, 2.5, 3, 4, 5, 10, 15, 20, 25, 50, 100, 150, and 200 mg). In some embodiments, individual dosages may be formulated to contain the desired dosage amount depending upon the number of times the compound is administered per day.

Methods of Use

In some aspects, the present disclosure is directed to methods of treating diseases or disorders characterized or mediated by aberrant (e.g., dysfunctional or dysregulated) WDYHV1, GSPT1, or PFKFB4 activity, that entails administration of a therapeutically effective amount of a compound of formula (I), or a pharmaceutically acceptable salt or stereoisomer thereof, to a subject in need thereof. In some embodiments, the present disclosure is directed to a method of reducing the levels of WDYHV1, GSPT1, or PFKFB4 in a cell, either in vitro or in vivo, comprising contacting the cell with a compound of formula (I).

The diseases or disorders are characterized or mediated by aberrant activity of WDYHV1, GSPT1, or PFKFB4 (e.g., elevated levels of WDYHV1, GSPT1, or PFKFB4, or otherwise functionally abnormal WDYHV1, GSPT1, or PFKFB4 relative to a non-pathological state). A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the animal's state of health. In some embodiments, compounds of formula (I) may be useful in the treatment of cell proliferative diseases and disorders (e.g., cancer or benign neoplasms). As used herein, the term "cell proliferative disease or disorder" refers to the conditions characterized by deregulated or abnormal cell growth, or both, including noncancerous conditions such as neoplasms, precancerous conditions, benign tumors, and cancer.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" treatment according to the present disclosure may be "suffering from or suspected of suffering from" a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

Exemplary types of non-cancerous (e.g., cell proliferative) diseases or disorders that may be amenable to treatment with the compounds of the present disclosure include inflammatory diseases and conditions, autoimmune diseases, neurodegenerative diseases, heart diseases, viral diseases, chronic and acute kidney diseases or injuries, metabolic diseases, and allergic and genetic diseases.

Representative examples of specific non-cancerous diseases and disorders include rheumatoid arthritis, alopecia areata, lymphoproliferative conditions, autoimmune hematological disorders (e.g. hemolytic anemia, aplastic anemia, anhidrotic ectodermal dysplasia, pure red cell anemia and idiopathic thrombocytopenia), cholecystitis, acromegaly, rheumatoid spondylitis, osteoarthritis, gout, scleroderma, sepsis, septic shock, dacryoadenitis, cryopyrin associated periodic syndrome (CAPS), endotoxic shock, endometritis, gram-negative sepsis, keratoconjunctivitis sicca, toxic shock syndrome, asthma, adult respiratory distress syndrome, chronic obstructive pulmonary disease, chronic pulmonary inflammation, chronic graft rejection, hidradenitis suppurativa, inflammatory bowel disease, Crohn's disease, Behcet's syndrome, systemic lupus erythematosus, glomerulonephritis, multiple sclerosis, juvenile-onset diabetes, autoimmune uveoretinitis, autoimmune vasculitis, thyroiditis, Addison's disease, lichen planus, appendicitis, bullous pemphigus, *Pemphigus vulgaris, Pemphigus foliaceus*, paraneoplastic pemphigus, myasthenia gravis, immunoglobulin A nephropathy, Hashimoto's disease, Sjogren's syndrome, vitiligo, Wegener granulomatosis, granulomatous orchitis, autoimmune oophoritis, sarcoidosis, rheumatic carditis, ankylosing spondylitis, Grave's disease, autoimmune thrombocytopenic purpura, psoriasis, psoriatic arthritis, eczema, dermatitis herpetiformis, ulcerative colitis, pancreatic fibrosis, hepatitis, hepatic fibrosis, CD14 mediated sepsis, non-CD14 mediated sepsis, acute and chronic renal disease, irritable bowel syndrome, pyresis, restenosis, cervicitis, stroke and ischemic injury, neural trauma, acute and chronic pain, allergic rhinitis, allergic conjunctivitis, chronic heart failure, congestive heart failure, acute coronary syndrome, cachexia, malaria, leprosy, leishmaniasis, Lyme disease, Reiter's syndrome, acute synovitis, muscle degeneration, bursitis, tendonitis, tenosynovitis, herniated, ruptured, or prolapsed intervertebral disk syndrome, osteopetrosis, rhinosinusitis, thrombosis, silicosis, pulmonary sarcosis, bone resorption diseases, such as osteoporosis, fibromyalgia, AIDS and other viral diseases such as Herpes Zoster, Herpes Simplex I or II, influenza virus and cytomegalovirus, diabetes Type I and II, obesity, insulin resistance and diabetic retinopathy, 22q11.2 deletion syndrome, Angelman syndrome, Canavan disease, celiac disease, Charcot-Marie-Tooth disease, color blindness, Cri du chat, Down syndrome, cystic fibrosis, Duchenne muscular dystrophy, haemophilia, Klinefleter's syndrome, neurofibromatosis, phenylketonuria, Prader-Willi syndrome, sickle cell disease, Tay-Sachs disease, Turner syndrome, urea cycle disorders, thalassemia, otitis, pancreatitis, parotitis, pericarditis, peritonitis, pharyngitis, pleuritis, phlebitis, pneumonitis, uveitis, polymyositis, proctitis, interstitial lung fibrosis, dermatomyositis, atherosclerosis, arteriosclerosis, amyotrophic lateral sclerosis, asociality, varicosis, vaginitis, depression, and Sudden Infant Death Syndrome.

In some embodiments, the compounds may be useful in the treatment of neurodegenerative diseases and disorders. As used herein, the term "neurodegenerative diseases and disorders" refers to conditions characterized by progressive degeneration or death of nerve cells, or both, including problems with movement (ataxias), or mental functioning (dementias). Representative examples of such diseases and disorders include Alzheimer's disease (AD) and AD-related dementias, Parkinson's disease (PD) and PD-related dementias, prion disease, motor neuron diseases (MND), Huntington's disease (HD), Pick's syndrome, spinocerebellar ataxia (SCA), spinal muscular atrophy (SMA), primary progressive aphasia (PPA), amyotrophic lateral sclerosis (ALS), traumatic brain injury (TBI), multiple sclerosis (MS), dementias (e.g., vascular dementia (VaD), Lewy body dementia (LBD), semantic dementia, and frontotemporal lobar dementia (FTD).

In some embodiments, the compounds may be useful in the treatment of autoimmune diseases and disorders. As used herein, the term "autoimmune disease" refers to conditions where the immune system produces antibodies that attack normal body tissues. Representative examples of such diseases include Sjogren's syndrome, Hashimoto thyroiditis, rheumatoid arthritis, juvenile (type 1) diabetes, polymyositis, scleroderma, Addison disease, lupus including systemic lupus erythematosus, vitiligo, pernicious anemia, glomerulonephritis, pulmonary fibrosis, celiac disease, polymyalgia rheumatica, multiple sclerosis, ankylosing spondylitis, alopecia areata, vasculitis, and temporal arteritis.

In other embodiments, the methods are directed to treating subjects having cancer. Broadly, the compounds of the present disclosure may be effective in the treatment of carcinomas (solid tumors including both primary and metastatic tumors), sarcomas, melanomas, and hematological cancers (cancers affecting blood including lymphocytes, bone marrow and/or lymph nodes) such as leukemia, lymphoma and multiple myeloma. Adult tumors/cancers and pediatric tumors/cancers are included. The cancers may be vascularized, or not yet substantially vascularized, or non-vascularized tumors.

Representative examples of cancers include adrenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, gestational trophoblastic tumor glioma, cerebellar astrocytoma, cerebral astrocytoma/malignant glioma, ependymoma, medulloblastoma, supratentorial primitive neuroectodermal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer (gastric cancer), small intestine cancer, gastrointestinal carcinoid tumor, gastrointestinal stromal tumor (GIST)), cholangiocarcinoma, germ cell tumor, ovarian germ cell tumor, head and neck cancer, neuroendocrine tumors, Hodgkin's lymphoma, Ann Arbor stage III and stage IV childhood Non-Hodgkin's lymphoma, ROS1-positive refractory Non-Hodgkin's lymphoma, leukemia, lymphoma, multiple myeloma, hypopharyngeal cancer, intraocular melanoma, ocular cancer, islet cell tumors (endocrine pancreas), renal cancer (e.g., Wilm's Tumor, renal cell carcinoma), liver cancer, lung cancer (e.g., non-small cell lung cancer and small cell lung cancer), ALK-positive anaplastic large cell lymphoma, ALK-positive advanced malignant solid neoplasm, Waldenstrom's macroglobulinema, melanoma, intraocular (eye) melanoma, merkel cell carcinoma, mesothelioma, metastatic squamous neck cancer with occult primary, multiple endocrine neoplasia (MEN), myelodysplastic syndromes, myelodysplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, metastatic anaplastic thyroid cancer, undifferentiated thyroid cancer, papillary thyroid cancer, pituitary tumor, plasma cell neoplasm/multiple myeloma, pleuropulmonary blastoma, prostate cancer, retinoblastoma, rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, juvenile xanthogranuloma, transitional cell cancer of the renal pelvis and ureter and other urinary organs, urethral cancer, gestational trophoblastic tumor, vaginal cancer, vulvar cancer, hepatoblastoma, rhabdoid tumor, and Wilms tumor.

Sarcomas that may be treatable with the compounds of the present disclosure include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue), mesenchymous or mixed mesodermal tumor (mixed connective tissue types), and histiocytic sarcoma (immune cancer).

In some embodiments, methods of the present disclosure entail treatment of subjects having cell proliferative diseases or disorders of the hematological system, liver, brain, lung, colon, pancreas, prostate, ovary, breast, skin, and endometrium.

As used herein, "cell proliferative diseases or disorders of the hematological system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, metastatic pancreatic adenocarcinoma, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, leukemia, including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the liver may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), adenocarcinoma, small cell carcinoma, large cell carcinoma, squamous cell carcinoma, and mesothelioma. Lung cancer can include "scar carcinoma", bronchioveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types). In some embodiments, a compound of the present disclosure may be used to treat non-metastatic or metastatic lung cancer (e.g., NSCLC, ALK-positive NSCLC, NSCLC harboring ROS1 rearrangement, lung adenocarcinoma, and squamous cell lung carcinoma).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polyposis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting cells of the endometrium. Cell proliferative disorders of the endometrium may include a precancer or precancerous condition of the endometrium, benign growths or lesions of the endometrium, endometrial cancer, and metastatic lesions in tissue and organs in the body other than the endometrium. Cell proliferative disorders of the endometrium may include hyperplasia, metaplasia, and dysplasia of the endometrium.

In some embodiments, the cancer is characterized by a solid tumor. In some embodiments, the cancer is selected from bladder cancer, colorectal cancer, breast cancer, brain cancer, endometrial cancer, head and neck cancer, gastrointestinal cancer, lung cancer, ovarian cancer, prostate cancer, uterine cancer, cervical cancer, hepatocellular carcinoma, lung cancer, liposarcoma, and melanoma. In some embodiments, the cancer is a hematological cancer. In some embodiments, the hematological cancer is selected from leukemia (e.g., acute myeloid leukemia), lymphoma, and myeloma.

The compounds of formula (I) may be administered to a patient, e.g., a cancer patient, as a monotherapy or by way of combination therapy. Therapy may be "front/first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which were unsuccessful or partially successful but who became intolerant to the treatment. Therapy may also be given as an adjuvant treatment, i.e., to prevent reoccurrence of cancer in patients with no currently detectable disease or after surgical removal of a tumor. Thus, in some embodiments, the compounds may be administered to a patient who has received another therapy, such as chemotherapy, radioimmunotherapy, surgical therapy, immunotherapy, radiation therapy, targeted therapy, or any combination thereof.

The methods of the present disclosure may entail administration of compounds of formula (I) or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks.

In some embodiments, the frequency of administration ranges from about once a day for 1, 2, 3, 4, 5, or 6 weeks, and in other embodiments entails a 28-day cycle which includes daily administration for 3 weeks (21 days) followed by a 7-day "off" period. In other embodiments, the compound may be dosed twice a day (BID) over the course of two and a half days (for a total of 5 doses) or once a day (QD) over the course of two days (for a total of 2 doses). In other embodiments, the compound may be dosed once a day (QD) over the course of five days.

Combination Therapy

Compounds of formula (I) may be used in combination or concurrently with at least one other active agent, e.g., anti-cancer agent or regimen, in treating diseases and disorders. The terms "in combination" and "concurrently" in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second compound, the first of the two compounds is, in some cases, still detectable at effective concentrations at the site of treatment. The sequence and time interval may be determined such that they can act together (e.g., synergistically) to provide an increased benefit than if they were administered otherwise. For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of a compound of formula (I) in combination with one or more additional therapeutics known for use in treating the disease or condition (e.g., cancer). The dosage of the additional anticancer therapeutic may be the same or even lower than known or recommended doses. See, Hardman et al., eds., *Goodman & Gilman's The Pharmacological Basis of Therapeutics,* 10th ed., McGraw-Hill, New York, 2001; Physician's Desk Reference 60th ed., 2006. For example, anti-cancer agents that may be suitable for use in combination with the compounds of formula (I) are known in the art. See, e.g., U.S. Pat. No. 9,101,622 (Section 5.2 thereof) and U.S. Pat. No. 9,345,705 B2 (Columns 12-18 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bifunctional antibodies) and CAR-T therapy.

In some embodiments, a compound of formula (I) and the additional (e.g., anticancer) therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more (e.g., anticancer) therapeutics may be administered within the same patient visit.

In some embodiments involving cancer treatment, the compound of formula (I) and the additional anti-cancer agent or therapeutic are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

In some embodiments, and depending on the particular cancer being treated, the compound of the present disclosure may be used in combination with at least one other anticancer agent such as Paclitaxel (e.g., ovarian cancer, breast cancer, lung cancer, Kaposi sarcoma, cervical cancer, and pancreatic cancer), Topotecan (e.g., ovarian cancer and lung cancer), Irinotecan (e.g., colon cancer, and small cell lung cancer), Etoposide (e.g., testicular cancer, lung cancer, lymphomas, and non-lymphocytic leukemia), Vincristine (e.g., leukemia), Leucovorin (e.g., colon cancer), Altretamine (e.g., ovarian cancer), Daunorubicin (e.g., acute myeloid leukemia (AML), acute lymphocytic leukemia (ALL), chronic myelogenous leukemia (CML), and Kaposi's sarcoma), Trastuzumab (e.g., breast cancer, stomach cancer, and esophageal cancer), Rituximab (e.g., non-Hodgkin's lymphoma), Cetuximab (e.g., colorectal cancer, metastatic non-small cell lung cancer and head and neck cancer), Pertuzumab (e.g., metastatic HER2-positive breast cancer), Alemtuzumab (e.g., chronic lymphocytic leukemia (CLL), cutaneous T-cell lymphoma (CTCL) and T-cell lymphoma), Panitumumab (e.g., colon and rectum cancer), Tamoxifen (e.g., breast cancer), Fulvestrant (e.g., breast cancer), Letrazole (e.g., breast cancer), Exemestane (e.g., breast cancer), Azacytidine (e.g., myelodysplastic syndromes), Mitomycin C (e.g., gastrointestinal cancers, anal cancers, and breast cancers), Dactinomycin (e.g., Wilms tumor, rhabdomyosarcoma, Ewing's sarcoma, trophoblastic neoplasm, testicular cancer, and ovarian cancer), Erlotinib (e.g., non-small cell lung cancer and pancreatic cancer), Sorafenib (e.g., kidney cancer and liver cancer), Temsirolimus (e.g., kidney cancer), Bortezomib (e.g., multiple myeloma and mantle cell lymphoma), Pegaspargase (e.g., acute lymphoblastic leukemia), Cabometyx (e.g., hepatocellular carcinoma, medullary thyroid cancer, and renal cell carcinoma), Pembrolizumab (e.g., cervical cancer, gastric cancer, hepatocellular carcinoma, Hodgkin's lymphoma, melanoma, Merkel cell carcinoma, non-small cell lung cancer, urothelial carcinoma, and squamous cell carcinoma of the head and neck), Nivolumab (e.g., colorectal cancer, hepatocellular carcinoma, melanoma, non-small cell lung cancer, renal cell carcinoma, small cell lung cancer, and urothelial carcinoma), Regorafenib (e.g., colorectal cancer, gastrointestinal stromal tumor, and hepatocellular carcinoma), Cemiplimab (e.g., cutaneous squamous cell carcinoma (CSCC)), Avelumab (e.g., Merkel cell carcinoma, urothelial carcinoma, and renal cell carcinoma), Durvalumab (e.g., bladder and lung cancer), Atezolizumab (e.g., urothelial carcinoma, non-small cell lung cancer (NSCLC), triple-negative breast cancer (TNBC), small cell lung cancer (SCLC), and heptatocellular carcinoma (HCC)), and Ipilimumab (e.g., melanoma, non-small cell lung carcinoma (NSCLC), small cell lung cancer (SCLC), bladder cancer, and prostate cancer).

Pharmaceutical Kits

The present compounds and/or compositions containing them may be assembled into kits or pharmaceutical systems. Kits or pharmaceutical systems according to this aspect of the disclosure include a carrier or package such as a box, carton, tube or the like, having in close confinement therein one or more containers, such as vials, tubes, ampoules, or bottles, which contain a compound of formula (I) or a pharmaceutical composition thereof. The kits or pharmaceutical systems of the disclosure may also include printed instructions for using the compounds and compositions.

These and other aspects of the present disclosure will be further appreciated upon consideration of the following Examples, which are intended to illustrate certain embodiments of the disclosure but are not intended to limit its scope, as defined by the claims.

EXAMPLES

These and other aspects of the present disclosure will be further appreciated upon consideration of the following Examples, which are intended to illustrate certain particular embodiments of the disclosure but are not intended to limit its scope, as defined by the claims.

General Methods

Unless otherwise indicated, reagents and solvents were used as received from commercial suppliers. All reactions were monitored using a Shimadzu® LC-20AD high performance liquid chromatography/mass spectrometry (HPLC/MS) system using Kinetex® BEH C18 column (2.1×30 mm, 5 μm particle size). Detection methods were diode array (DAD). MS mode was positive electrospray ionization. MS range was 100-1000. HPLC method A: the gradient was 5-95% B in 1.50 min. 5% B in 0.01 min, 5-95% B (0.01-0.70 min), 95% B (0.70-1.15 min), 5% B in 1.16 min with a hold at 5% B for 0.34 min; solvent A=0.04% trifluoroacetic acid in $H_2O$; solvent B=0.02% trifluoroacetic acid in acetonitrile; flow rate: 1.5 mL/min. Purification of reaction products was carried out by flash chromatography using CombiFlash®Rf with Biotage-Isolera® normal-phase silica flash columns; or Waters® high performance liquid chromatography (HPLC) system using Phenomenex Luna C18 (80*30 mm*3 μm): solvent gradient 0% to 99% acetonitrile in $H_2O$ (0.1% trifluoroacetic acid (TFA) as additive); flow rate: 25 mL/min, or Phenomenex Luna C18 (100*30 mm*5 μm): solvent gradient 0% to 99% acetonitrile in $H_2O$ (0.2% formic acid (FA) as additive); flow rate: 25 mL/min, or Phenomenex Luna C18 (80*30 mm*3 μm): solvent gradient 0% to 99% acetonitrile in $H_2O$ (0.04% hydrochloric acid (HCl) as additive); flow rate: 25 mL/min. The purity of all compounds was over 95% and was analyzed with Shimadzu® HPLC system. $^1H$ NMR and $^{13}C$ NMR spectra were obtained using Bruker Avance III spectrometers (400 MHz for $^1H$, and 100 MHz for $^{13}C$). Chemical shifts are reported relative to deuterated methanol (δ=3.31) or dimethyl sulfoxide (DMSO) (δ=2.50) for $^1H$ NMR. Spectra are given in ppm (δ) and as br=broad, s=singlet, d=doublet, t=triplet, q=quartet, m=multiplet and coupling constants (J) are reported in Hertz. Room temperature is indicated as "rt", hours are indicated as "hr" or "h", "aqueous" is indicated as "aq.", minutes are indicated as "min" and seconds are indicated as "s".

Example 1: Synthesis of N-(4-acetamidophenyl)-N-fluorosulfonyl-sulfamoyl Fluoride

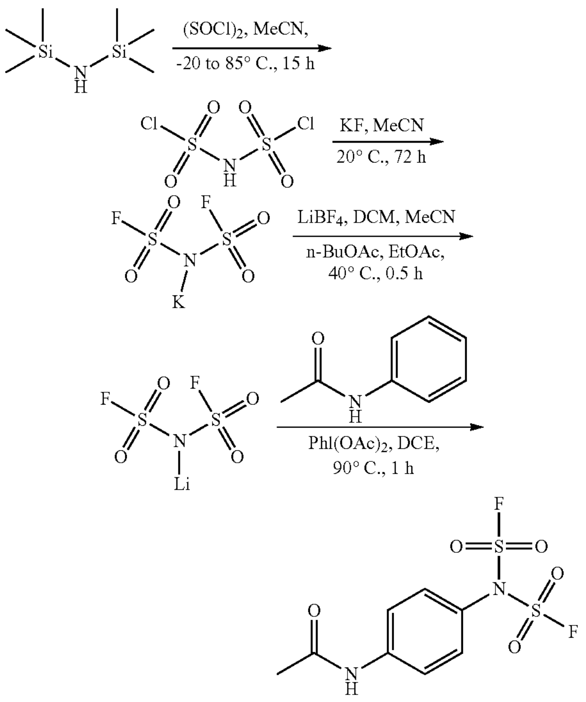

Synthesis of N-chlorosulfonylsulfamoyl Chloride

To a solution of sulfuryl chloride (20.9 g, 154.90 mmol) in $CH_3CN$ (50 mL) was added hexamethyldisilazane (5.0 g, 30.98 mmol) under $N_2$ at −20° C. The mixture was stirred at 20° C. for 12 hr. The reaction was then heated to 85° C. and stirred for 3 hr. The reaction mixture was concentrated under reduced pressure to afford the crude title compound (3.5 g) as a light yellow solid, which was used without further purification.

Synthesis of [bis-(fluorosulfonyl) amino] potassium

To a solution of N-chlorosulfonylsulfamoyl chloride (3.5 g, 16.35 mmol) in $CH_3CN$ (100 mL) was added KF (5.7 g, 98.11 mmol). The suspension was stirred at 20° C. for 72 hr. The reaction was filtered and concentrated under reduced pressure to afford the crude title compound (700 mg, 19.53% yield) as a light-yellow oil, which was used without further purification.

Synthesis of [bis(fluorosulfonyl) amino] lithium

To a solution of [bis(fluorosulfonyl) amino] potassium (700 mg, 3.19 mmol) in 10 mL of mixed solvents [EtOAc (4 mL), n-butyl acetate (3 mL), $CH_3CN$ (3 mL)] was added a solution of lithium tetrafluoroborate (299 mg, 3.19 mmol) in 10 mL of mixed solvents [DCM (1 mL), EtOAc (3 mL), butyl acetate (3 mL), $CH_3CN$ (3 mL)]. The mixture was stirred at 40° C. for 30 min. The reaction was then filtered and concentrated under reduced pressure to afford the crude title compound (1.0 g) as a yellow oil, which was used without further purification.

Synthesis of N-(4-acetamidophenyl)-N-fluorosulfonyl-sulfamoyl fluoride

To a solution of [bis(fluorosulfonyl)amino] lithium (498 mg, 2.66 mmol) and (diacetoxyiodo)benzene (643 mg, 2.00 mmol) in dichloroethane (DCE, 4 mL) under reflux was added N-phenylacetamide (180 mg, 1.33 mmol) in DCE (5 mL) dropwise over a period of three min. The mixture was stirred at 90° C. for 1 hr. The reaction mixture was concentrated under reduced pressure to afford the crude title compound as a white solid, which was used without further purification.

Example 2: Synthesis of 2-(2,6-dioxopiperidin-3-yl)-3-oxoisoindolin-5-yl sulfurofluoridate (1)

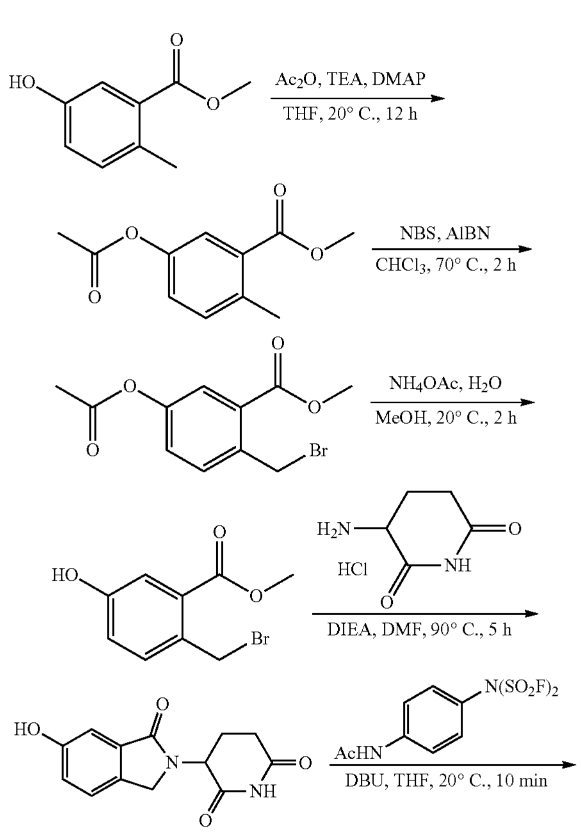

-continued

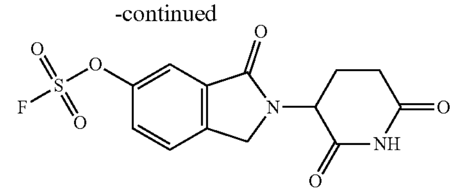

1

Synthesis of methyl 5-acetoxy-2-methyl-benzoate

To a solution of methyl 5-hydroxy-2-methyl-benzoate (4.5 g, 27.08 mmol) in THF (100 mL) were added triethylamine (8.2 g, 81.24 mmol), dimethylaminopyridine (331 mg, 2.71 mmol) and $Ac_2O$ (4.15 g, 40.62 mmol). The reaction was stirred at 20° C. for 12 hr. The reaction was then quenched with aq. 6 N HCl until pH reached 1-3 and then further diluted with $H_2O$ (100 mL). The reaction was then extracted with EtOAc (100 mL×3). The layers were separated, and the combined organic layers were dried over $Na_2SO_4$, filtered and concentrated under reduced pressure to give the crude title compound (6.2 g) as a light-yellow liquid, which was used without further purification. MS ($M+H^+$): 209.1.

Synthesis of methyl 5-acetoxy-2-(bromomethyl)benzoate

To a solution of methyl 5-acetoxy-2-methyl-benzoate (5.7 g, 27.38 mmol) in $CHCl_3$ (110 mL) were added N-bromosuccinimide (5.4 g, 30.11 mmol) and AIBN (450 mg, 2.74 mmol). The mixture was stirred at 70° C. for 2 hr under $N_2$. The reaction was quenched by addition of $H_2O$ (150 mL). The layers were separated, and the aq. layer was extracted with EtOAc (150 mL×3). The combined organic layers were dried over $Na_2SO_4$, filtered and concentrated under reduced pressure to give a residue that was purified by column chromatography (petroleum ether/ethyl acetate=3/1 to 2/1) to afford the title compound (6.5 g, 22.64 mmol, 82.70% yield) as a light-yellow oil. MS ($M+H^+$): 288.9.

Synthesis of methyl 2-(bromomethyl)-5-hydroxy-benzoate

To a solution of methyl 5-acetoxy-2-(bromomethyl) benzoate (3.5 g, 12.19 mmol) in MeOH (32 mL) and $H_2O$ (8 mL) was added $NH_4OAc$ (21.6 g, 280.38 mmol). The reaction was stirred at 20° C. for 2 hr. The reaction mixture was then quenched by addition of aq. sat. $NaHCO_3$ (50 mL) solution, and then the aq. phase was extracted with EtOAc (50 mL×3). The combined organic layers were washed with brine (20 mL), dried over $Na_2SO_4$, filtered and concentrated under reduced pressure to give a residue. The residue was purified by column chromatography (petroleum ether/ethyl acetate=3/1 to 2/1) to afford the title compound (1.3 g, 5.30 mmol, 44% yield) as a white solid. $^1H$ NMR: (400 MHz, DMSO-$d_6$) δ=9.91 (s, 1H), 7.32 (d, J=8.8 Hz, 1H), 7.28 (d, J=4.4 Hz, 1H), 6.98 (dd, J=2.4, 8.4 Hz, 1H), 5.24 (s, 2H), 3.80 (s, 3H).

Synthesis of 3-(6-hydroxy-1-oxo-isoindolin-2-yl) piperidine-2,6-dione

To a solution of methyl 2-(bromomethyl)-5-hydroxy-benzoate (1.2 g, 4.90 mmol) and 3-aminopiperidine-2,6-dione (806 mg, 4.90 mmol) in dimethylformamide (30 mL) was added N-diisopropylethylamine (DIEA, 1.90 g, 14.69 mmol). The mixture was then stirred at 90° C. for 5 hr. The reaction mixture was concentrated under reduced pressure to give a residue. The residue was purified by column chromatography (ethyl acetate/methanol=1/0 to 10/1) to afford the title compound (500 mg, 1.56 mmol, 33% yield) as a light yellow solid. MS ($M+H^+$): 261.1.

Synthesis of 2-(2,6-dioxo-3-piperidyl)-6-fluorosulfonyloxy-1-oxo-isoindoline (1)

1

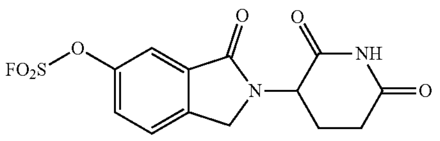

To a solution of 3-(6-hydroxy-1-oxo-isoindolin-2-yl)piperidine-2,6-dione (65 mg, 249.76 μmol) in THF (2 mL) were added N-(4-acetamidophenyl)-N-fluorosulfonyl-sulfamoyl fluoride (94 mg, 300 μmol) and 1,8-diazabicyclo[5.4.0]undec-7-ene (DBU, 84 mg, 550 μmol). The reaction was stirred at 20° C. for 10 min. The reaction was then quenched by addition of $H_2O$ (5 mL), and then the layers were separated and the aq. layer extracted with EtOAc (10 mL×3). The combined organic layers were washed with brine (10 mL), dried over $Na_2SO_4$, filtered and concentrated under reduced pressure to give a residue. The residue was purified by prep-HPLC to afford the title compound (5 mg, 14.0 μmol, 5.6% yield) as a white solid. MS ($M+H^+$): 342.9; $^1H$ NMR: (400 MHz, DMSO-$d_6$) δ=11.04 (s, 1H), 7.98 (d, J=2.2 Hz, 1H), 7.91-7.83 (m, 2H), 5.15 (dd, J=4.8, 13.4 Hz, 1H), 4.59-4.38 (m, 2H), 2.97-2.85 (m, 1H), 2.69-2.56 (m, 1H), 2.45-2.31 (m, 1H), 2.09-1.98 (m, 1H).

Example 3: Synthesis of 2-(2,6-dioxopiperidin-3-yl)-1-oxoisoindolin-5-yl sulfurofluoridate (2)

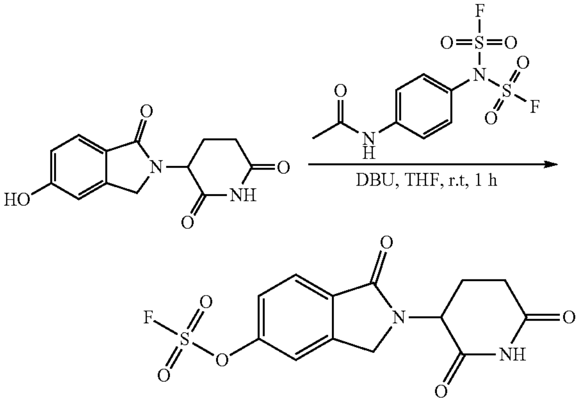

2

To a solution of 3-(5-hydroxy-1-oxo-isoindolin-2-yl)piperidine-2,6-dione (40 mg, 0.15 mmol) and N-(4-acetamidophenyl)-N-fluorosulfonyl-sulfamoyl fluoride (51 mg, 0.16 mmol) in THF (1 mL) was added 1,8-diazabicyclo[5.4.0]undec-7-ene (DBU, 23 mg, 0.15 mmol). The mixture was stirred at 20° C. for one hr. After completion of the reaction, the reaction was concentrated under reduced pressure to give a residue, which was purified by prep-HPLC to afford the title compound (1.4 mg, 0.004 mmol, 3% yield) as a white solid. MS ($M+H^+$): 343.0; $^1H$ NMR (400 MHz, DMSO-$d_6$) δ=11.03 (s, 1H), 7.99-7.92 (m, 2H), 7.81-7.71 (m, 1H), 5.14 (dd, 1=5.1, 13.4 Hz, 1H), 4.60-4.54 (m, 1H), 4.47-4.40 (m, 1H), 2.98-2.86 (m, 1H), 2.65-2.58 (m, 1H), 2.39-2.38 (m, 1H), 2.09-1.99 (m, 1H).

Example 4: Synthesis of 2-(2,6-dioxopiperidin-3-yl)-3-oxoisoindoline-5-sulfonyl fluoride (3)

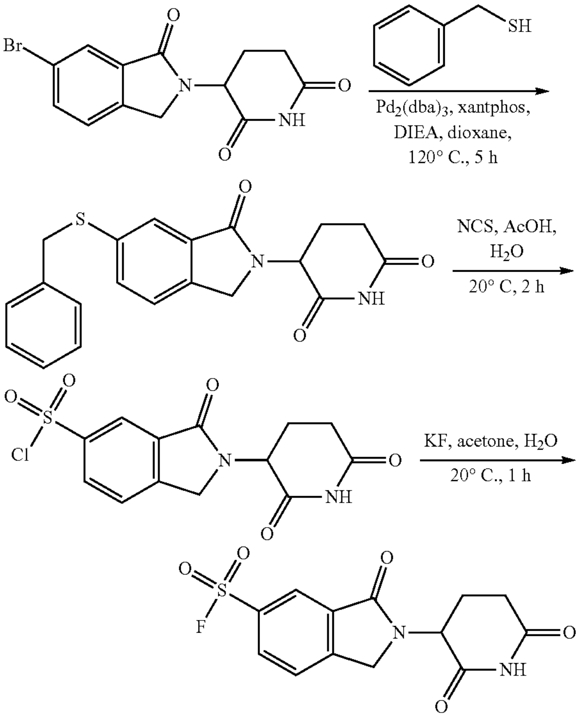

3

Synthesis of 3-(6-(benzylthio)-1-oxoisoindolin-2-yl)piperidine-2,6-dione

To a solution of 3-(6-bromo-1-oxo-isoindolin-2-yl)piperidine-2,6-dione (0.8 g, 2.48 mmol) and phenylmethanethiol (308 mg, 2.48 mmol) in dioxane (12 mL) was added DIEA (640 mg, 4.95 mmol). The mixture was degassed and purged with $N_2$ three times. Then $Pd_2(dba)_3$ (136 mg, 148.54 μmol) and xantphos (172 mg, 297.08 μmol) were added, and the mixture was degassed and purged with $N_2$ three times and then stirred at 120° C. for 5 hr under $N_2$. The reaction was cooled to rt, filtered and the solid collected was washed with $H_2O$ (50 mL) and EtOAc (50 mL). The filter cake was further dried under vacuum to yield the crude title compound (900 mg) as a gray solid, which was used without further purification. MS ($M+H^+$): 367.1.

Synthesis of 2-(2,6-dioxopiperidin-3-yl)-3-oxoisoindoline-5-sulfonyl chloride

To a solution of 3-(6-benzylsulfanyl-1-oxo-isoindolin-2-yl)piperidine-2,6-dione (0.4 g, 1.09 mmol) in $H_2O$ (2 mL)

and AcOH (18 mL) was added N-chlorosuccinimide (NCS, 437 mg, 3.27 mmol). The reaction was stirred at 20° C. for 2 hr, then diluted with $H_2O$ (20 mL) and filtered. The filter cake was washed with water (20 mL) and dried further under reduced pressure to yield the crude title compound (0.2 g) as a yellow solid, which was used without further purification. MS ($M+H^+$): 343.0.

Synthesis of 2-(2,6-dioxopiperidin-3-yl)-3-oxoisoindoline-5-sulfonyl fluoride (3)

3

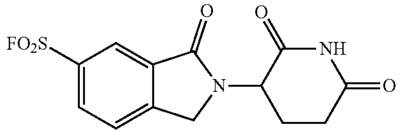

To a solution of 2-(2,6-dioxo-3-piperidyl)-3-oxo-isoindoline-5-sulfonyl chloride (0.2 g, 583.51 μmol) in acetone (10 mL) and $H_2O$ (10 mL) was added KF (509 mg, 8.75 mmol). The reaction was stirred at 20° C. for 1 h. The reaction mixture was diluted with $H_2O$ (50 mL) and filtered. The filter cake was washed with water (20 mL) and dried under reduced pressure to give a residue. The residue was purified by prep-HPLC to yield the title compound (90 mg, 272 μmol, 47% yield) as a white solid. MS ($M+H^+$): 326.9; $^1H$ NMR: (400 MHz, DMSO-$d_6$) δ=11.06 (s, 1H), 8.41 (dd, J=8.13, 1.63 Hz, 1H), 8.33 (s, 1H), 8.07 (d, J=8.13 Hz, 1H), 5.19 (dd, J=13.32, 5.07 Hz, 1H), 4.65-4.74 (m, 1H), 4.53-4.61 (m, 1H), 2.82-3.00 (m, 1H), 2.62 (br d, J=17.76 Hz, 1H), 2.37-2.47 (m, 1H), 2.00-2.08 (m, 1H).

Example 5: Synthesis of 2-(2,6-dioxopiperidin-3-yl)-1-oxoisoindoline-5-sulfonyl fluoride (4)

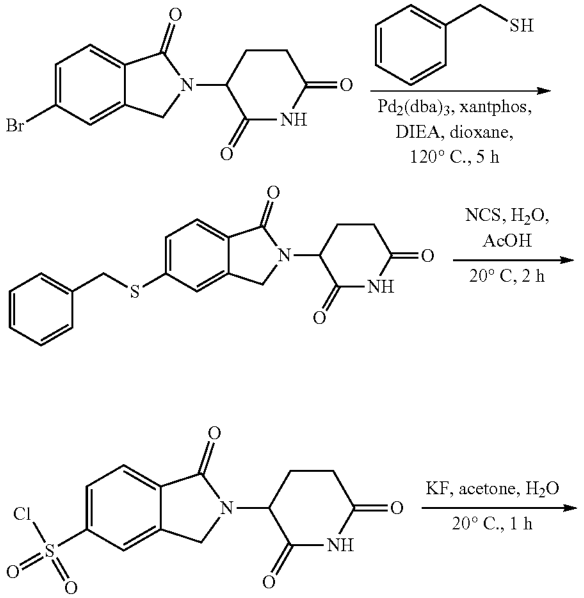

-continued

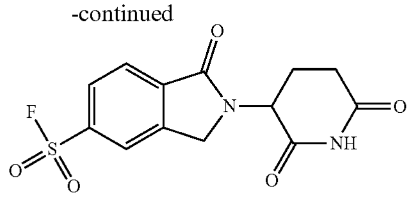

4

Synthesis of 3-(5-(benzylthio)-1-oxoisoindolin-2-yl)piperidine-2,6-dione

To a solution of 3-(5-bromo-1-oxo-isoindolin-2-yl)piperidine-2,6-dione (1 g, 3.09 mmol) and phenylmethanethiol (385 mg, 3.09 mmol) in dioxane (20 mL) was added DIEA (800 mg, 6.19 mmol). The reaction was degassed and purged with $N_2$ three times. Then $Pd_2(dba)_3$ (170 mg, 185.68 μmol) and xantphos (215 mg, 371.35 μmol) was added. The mixture was degassed and purged with $N_2$ three times and stirred at 120° C. for 5 hr under $N_2$. The reaction was then cooled to rt, filtered and the solid was collected and washed with $H_2O$ (20 mL) and EtOAc (20 mL). The filter cake was dried under reduced pressure to yield the crude title compound (1 g) as a white solid, that was used without further purification. MS ($M+H^+$): 367.2.

Synthesis of 2-(2,6-dioxopiperidin-3-yl)-1-oxoisoindoline-5-sulfonyl chloride

To a solution of 3-(5-benzylsulfanyl-1-oxo-isoindolin-2-yl)piperidine-2,6-dione (0.1 g, 272.90 μmol) in $H_2O$ (0.5 mL) and AcOH (4.5 mL) was added NCS (109 mg, 819 μmol). The reaction was stirred at 20° C. for 2 hr, then diluted with $H_2O$ (20 mL) and filtered. The filter cake was washed with water (20 mL) and dried further under reduced pressure to yield the crude title compound as a yellow solid, which was used without further purification. MS ($M+H^+$): 343.3.

Synthesis of 2-(2,6-dioxopiperidin-3-yl)-1-oxoisoindoline-5-sulfonyl fluoride (4)

4

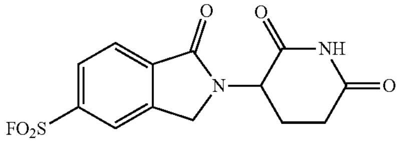

To a solution of 2-(2,6-dioxo-3-piperidyl)-1-oxo-isoindoline-5-sulfonyl chloride (90 mg, 262.58 μmol) in acetone (5 mL) and $H_2O$ (5 mL) was added KF (229 mg, 3.94 mmol). The mixture was stirred at 20° C. for 1 hr and then purified by prep-HPLC to yield the title compound (43 mg, 131 μmol, 50% yield) as a white solid. MS ($M+H^+$); 326.8; $^1H$ NMR (400 MHz, DMSO-$d_6$) δ=2.01-2.13 (m, 1H) 2.45 (br dd, J=13.13, 4.38 Hz, 1H) 2.63 (br d, J=18.14 Hz, 1H) 2.87-2.99 (m, 1H) 4.50-4.58 (m, 1H) 4.62-4.70 (m, 1H) 5.20 (dd, J=13.26, 5.00 Hz, 1H) 8.11 (d, J=8.13 Hz, 1H) 8.28 (d, J=8.00 Hz, 1H) 8.51 (s, 1H) 11.07 (s, 1H).

Example 6: Synthesis of 3-(1-oxo-6-(vinylsulfonyl) isoindolin-2-yl)piperidine-2,6-dione (5)

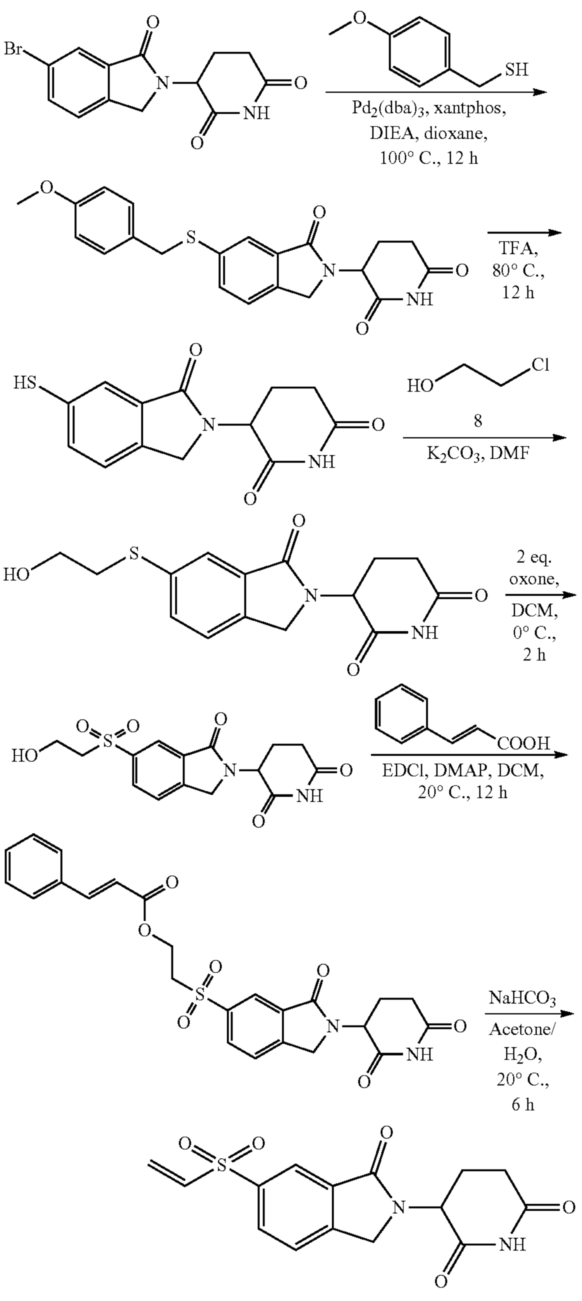

5

Synthesis of 3-(6-((4-methoxybenzyl)thio)-1-oxoisoindolin-2-yl)piperidine-2,6-dione To a solution of 3-(6-bromo-1-oxo-isoindolin-2-yl)piperidine-2,6-dione (2.0 g, 6.19 mmol) and (4-methoxyphenyl) methanethiol (955 mg, 6.19 mmol) in 1,4-dioxane (30 mL) was added DIEA (1.6 g, 12.38 mmol). The reaction was degassed and purged with $N_2$ three times. Then xantphos (430 mg, 0.74 mmol) and Pd$_2$(dba)$_3$ (340 mg, 0.43 mmol) were added, and the mixture was degassed and purged with $N_2$ three times and stirred at 100° C. for 12 hr under $N_2$. The reaction mixture was then cooled to rt, diluted with $H_2O$ (10 mL) and EtOAc (10 mL). The solid precipitate was filtered and the filter cake was dried under vacuum to afford the title compound (2.42 g, 6.10 mmol, 99% yield) as a green solid, which was used without further purification. MS (M+H$^+$): 397.2.

Synthesis of 3-(6-mercapto-1-oxoisoindolin-2-yl) piperidine-2,6-dione

A solution of 3-[6-[(4-methoxyphenyl)methylsulfanyl]-1-oxo-isoindolin-2-yl]piperidine-2,6-dione (1.2 g, 3.03 mmol) in TFA (20 mL) was stirred at 80° C. for 12 hr. The reaction was concentrated under reduced pressure to give a crude residue, which was triturated with 10 mL of mixed solvents [petroleum ether (5 mL) and EtOAc (5 mL)] at 20° C. for 15 min. The solid residue was collected and dried to give the crude title compound (0.8 g, 2.90 mmol, 96% yield) as a green solid, that was used without further purification. MS (M+H$^+$): 277.1.

Synthesis of 3-(6-((2-hydroxyethyl)thio)-1-oxoisoindolin-2-yl)piperidine-2,6-dione To a solution of 3-(1-oxo-6-sulfanyl-isoindolin-2-yl)piperidine-2,6-dione (0.86 g, 2.49 mmol) and 2-bromoethanol (373 mg, 2.99 mmol) in DMF (5 mL) was added $K_2CO_3$ (688 mg, 4.98 mmol). The mixture was stirred at 20° C. for 0.5 hr. The reaction was concentrated under reduced pressure. The crude product was triturated with 10 mL of mixed solvents [DCM (5 mL) and EtOAc (5 mL)] at 20° C. for 15 min. The solid was filtered out, washed with water (2×20 mL) and dried under reduced pressure to yield the title compound (0.6 g, 1.87 mmol, 75% yield) as a brown solid, that was used without further purification. MS (M-W): 319.0.

Synthesis of 3-(6-((2-hydroxyethyl)sulfonyl)-1-oxoisoindolin-2-yl)piperidine-2,6-dione To a solution of 3-[6-(2-hydroxyethylsulfanyl)-1-oxo-isoindolin-2-yl]piperidine-2,6-dione (370 mg, 1.15 mmol) in EtOH (6 mL) and $H_2O$ (6 mL) was added oxone (1.4 g, 2.31 mmol). The mixture was stirred at 0° C. for two hr. The reaction was then diluted with $H_2O$ (10 mL) and extracted with EtOAc (20 mL×3). The combined organic layers were washed with brine (20 mL×2) and dried over anhydrous $Na_2SO_4$, and then filtered and concentrated under reduced pressure. The residue was purified by prep-HPLC to give the title compound (70 mg, 0.20 mmol, 17% yield) as a white solid. MS (M-W): 351.0.

Synthesis of 2-((2-(2,6-dioxopiperidin-3-yl)-3-oxoisoindolin-5-yl)sulfonyl)ethyl cinnamate To a solution of 3-[6-(2-hydroxyethylsulfonyl)-1-oxo-isoindolin-2-yl]piperidine-2,6-dione (70 mg, 0.20 mmol) in DCM (1 mL) were added N-(3-dimethylaminopropyl)-N'-ethylcarbodiimide hydrochloride (EDCI, 46 mg, 0.24 mmol) and DMAP (2 mg, 0.02 mmol) and (Z)-3-phenylprop-2-enoic acid (29 mg, 0.20 mmol). The reaction was stirred at 20° C. for 12 hr. The residue was then diluted with EtOAc (10 mL) and $H_2O$ (10 mL). Layers were separated and the aq. layer was extracted with EtOAc (20 mL×3). The combined organic layers were washed with brine (20 mL×2) and dried over anhydrous $Na_2SO_4$, filtered and concentrated under reduced pressure to give the title compound (120 mg) as a yellow oil, that was used without further purification. MS (M−H$^+$): 481.0.

Synthesis of 3-(1-oxo-6-(vinylsulfonyl)isoindolin-2-yl)piperidine-2,6-dione (5)

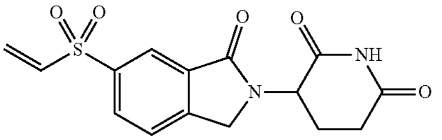

5

To a solution of 2-[2-(2,6-dioxo-3-piperidyl)-3-oxo-isoindolin-5-yl]sulfonylethyl 3-phenylprop-2-enoate (60 mg, 0.12 mmol) in acetone (0.5 mL) and $H_2O$ (0.5 mL) was added $NaHCO_3$ (16 mg, 0.19 mmol). The mixture was stirred at 20° C. for 6 hr. The reaction was filtered and diluted with $H_2O$ (10 mL) and extracted with EtOAc (20 mL×3). The combined organic layers were washed with brine (20 mL×2) and dried over anhydrous $Na_2SO_4$, filtered and concentrated under reduced pressure. The residue was purified by prep-HPLC to give the title compound (1 mg, 0.003 mmol, 3% yield) as a white solid. MS (M+H$^+$): 335.1. $^1$H NMR (400 MHz, DMSO-$d_6$) δ=11.04 (s, 1H), 8.13 (qd, J=1.9, 4.2 Hz, 2H), 7.93 (d, J=8.5 Hz, 1H), 7.24 (dd, J=9.8, 16.5 Hz, 1H), 6.43 (d, J=16.5 Hz, 1H), 6.27 (d, J=9.8 Hz, 1H), 5.17 (dd, J=5.1, 13.5 Hz, 1H), 4.67-4.58 (m, 1H), 4.55-4.44 (m, 1H), 2.98-2.86 (m, 1H), 2.64 (br s, 1H), 2.40-2.37 (m, 1H), 2.07-2.00 (m, 1H).

Example 7: Synthesis of N-(2-(2,6-dioxopiperidin-3-yl)-3-oxoisoindolin-5-yl)ethenesulfonamide (6)

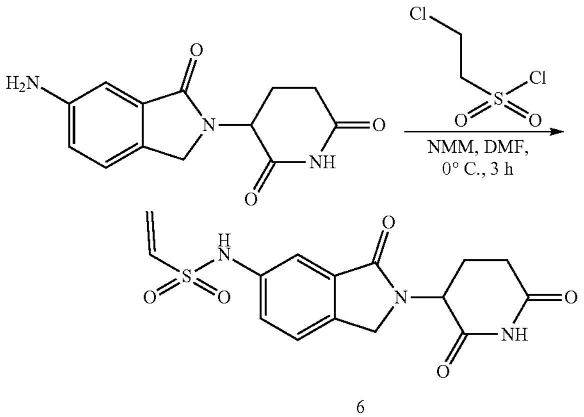

6

To a solution of 3-(6-amino-1-oxo-isoindolin-2-yl)piperidine-2,6-dione (0.1 g, 0.39 mmol) in DMF (1 mL) were added 4-methylmorpholine (NMM, 117 mg, 1.16 mmol) and 2-chloroethanesulfonyl chloride (69 mg, 0.42 mmol). The mixture was stirred at 0° C. for 3 h. The reaction was concentrated under reduced pressure to give a residue. The residue was purified by prep-HPLC to afford the title compound (14 mg, 0.04 mmol, 11% yield) as a white solid. MS (M+H$^+$); 350.1; $^1$H NMR (400 MHz, DMSO-$d_6$) δ=11.00 (s, 1H), 7.56 (d, J=8.2 Hz, 1H), 7.49 (d, J=1.9 Hz, 1H), 7.40 (dd, J=2.0, 8.2 Hz, 1H), 6.81 (dd, J=10.0, 16.4 Hz, 1H), 6.15-6.00 (m, 2H), 5.10 (dd, J=5.1, 13.2 Hz, 1H), 4.45-4.36 (m, 1H), 4.33-4.23 (m, 1H), 2.97-2.84 (m, 1H), 2.64-2.56 (m, 1H), 2.45-2.31 (m, 1H), 2.06-1.95 (m, 1H).

Example 8: Synthesis of 3-(6-((2H-1,2,3-triazol-2-yl)sulfonyl)-1-oxoisoindolin-2-yl)piperidine-2,6-dione (7)

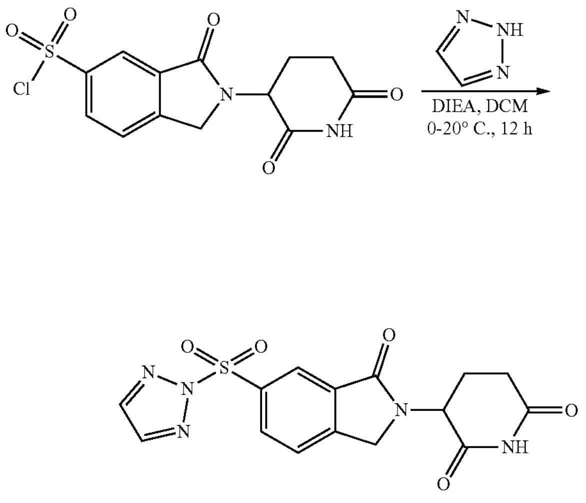

7

To a 0° C. solution of 2-(2,6-dioxo-3-piperidyl)-3-oxo-isoindoline-5-sulfonyl chloride (0.2 g, 583.51 μmol) in methylene chloride (DCM, 5 mL) were added DIEA (151 mg, 1.17 mmol) and 2H-triazole (202 mg, 2.92 mmol). The mixture was then stirred at 20° C. for 12 hr, and concentrated under reduced pressure. The residue was purified by prep-HPLC to afford the title compound (5 mg, 13.25 μmol, 50% yield) as a white solid. MS (M+H$^+$): 376.0; $^1$H NMR (400 MHz, DMSO-$d_6$) δ=11.03 (s, 1H), 8.31 (s, 2H), 8.27 (dd, J=1.9, 8.1 Hz, 1H), 8.15 (d, J=1.5 Hz, 1H), 7.96 (d, J=8.1 Hz, 1H), 5.14 (dd, J=5.1, 13.3 Hz, 1H), 4.67-4.58 (m, 1H), 4.54-4.45 (m, 1H), 2.98-2.84 (m, 1H), 2.60 (br d, J=17.6 Hz, 1H), 2.45-2.36 (m, 1H), 2.06-1.97 (m, 1H).

Example 9: Synthesis of 3-(6-((1H-1,2,4-triazol-1-yl)sulfonyl)-1-oxoisoindolin-2-yl)piperidine-2,6-dione (8)

8

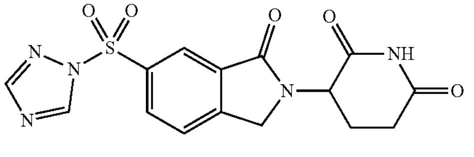

The title compound was prepared from 2-(2,6-dioxo-3-piperidyl)-3-oxo-isoindoline-5-sulfonyl chloride and 1,2,4-triazole using the method described in Example 8. MS (M+H$^+$): 376.0.

Example 10: Synthesis of 2-(2,6-dioxopiperidin-3-yl)-1-oxoisoindolin-4-yl sulfurofluoridate (9)
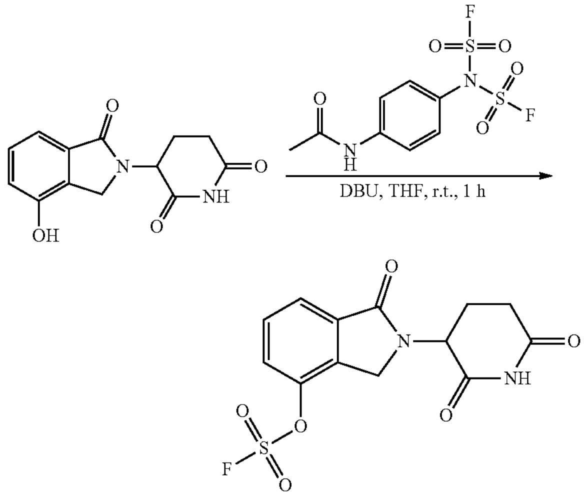
9
The title compound was prepared similarly as described in Example 3 (34% yield) as a white solid. MS (M+H$^+$): 343.1; $^1$H NMR (400 MHz, DMSO-$d_6$) δ=11.00 (s, 1H), 7.93-7.86 (m, 2H), 7.80-7.72 (m, 1H), 5.13 (dd, J=5.1, 13.1 Hz, 1H), 4.70-4.43 (m, 2H), 2.96-2.83 (m, 1H), 2.63-2.53 (m, 2H), 2.06-1.95 (m, 1H).
Example 11: Synthesis of 4-amino-2-(2,6-dioxo-3-piperidyl)-6-fluorosulfonyloxy-1-oxo-isoindoline (10)
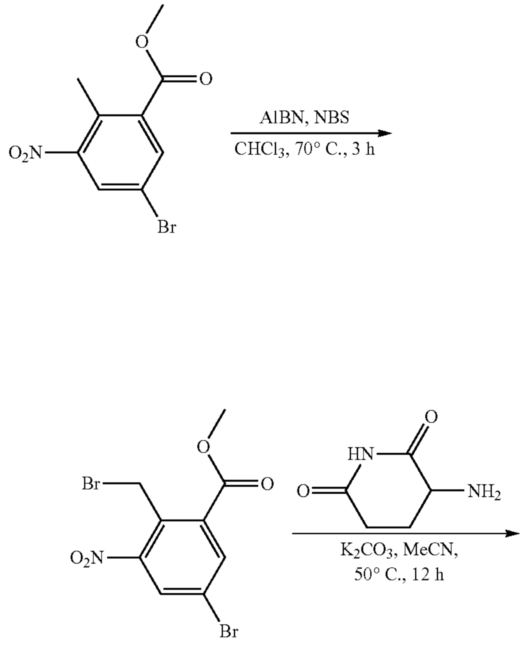
-continued
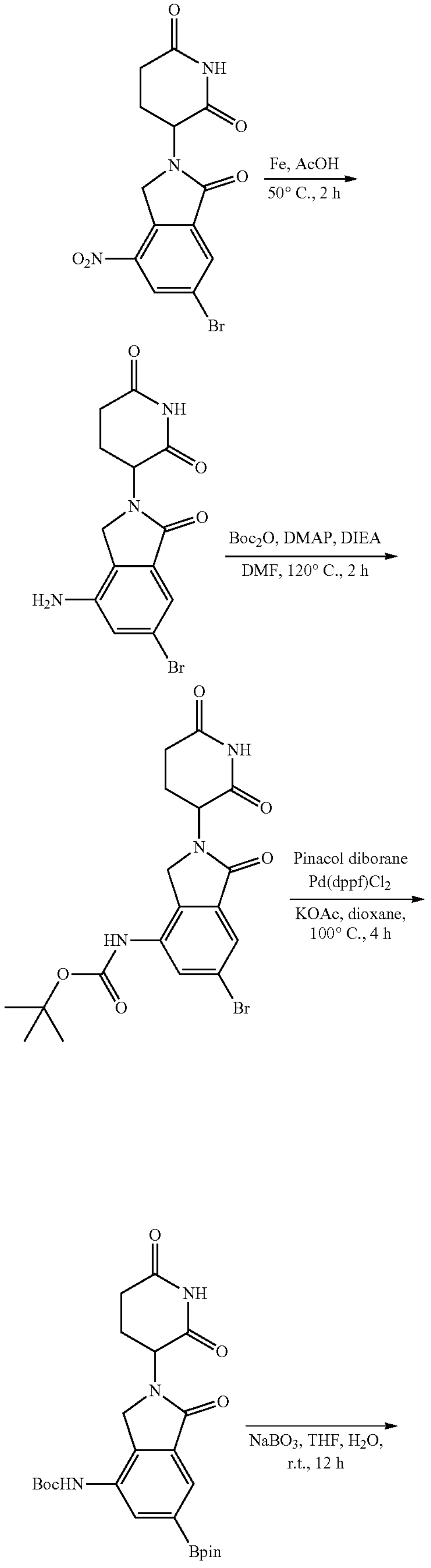

-continued

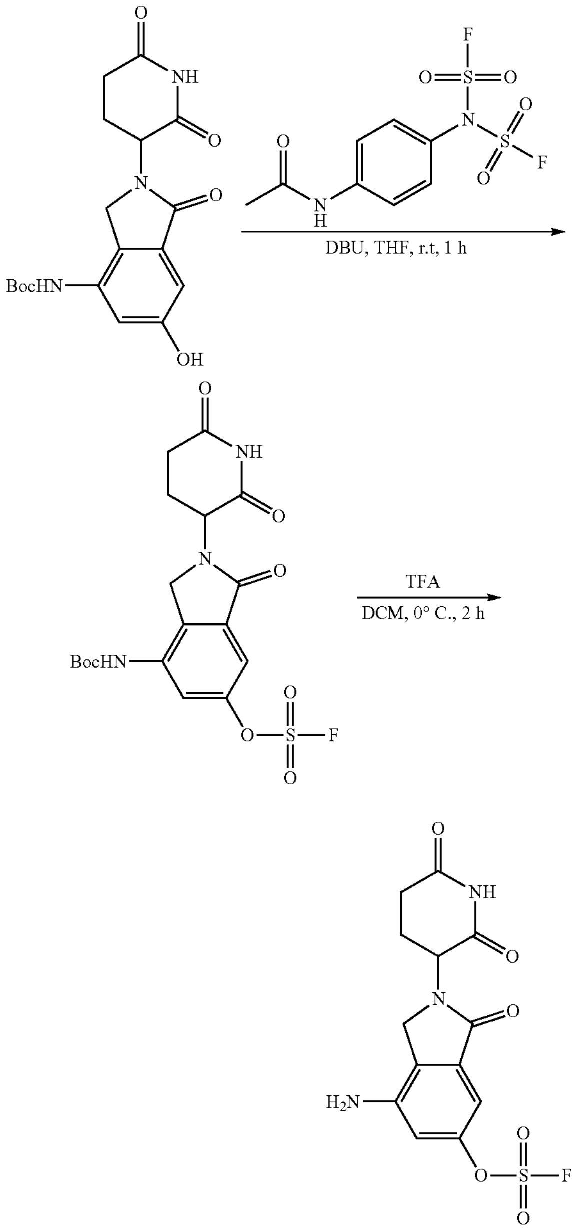

10

Synthesis of methyl 5-bromo-2-(bromomethyl)-3-nitro-benzoate

A solution of methyl 5-bromo-2-methyl-3-nitro-benzoate (25.00 g, 91.2 mmol), N-bromosuccinimide (NBS, 17.86 g, 100.34 mmol), azobisisobutyronitrile, (AIBN, 3.00 g, 18.24 mmol) in $CHCl_3$ (200 mL) was degassed and purged with $N_2$ three times, and then stirred at 70° C. for three hr under a nitrogen atmosphere. The reaction mixture was concentrated under reduced pressure to give a residue, which was purified by silica gel column chromatography (petroleum ether/ethyl acetate=1/0 to 20/1) to afford the title compound (29.76 g, 84.31 mmol, 60% purity, 56% yield) as a white solid that was used without further purification.

Synthesis of 3-(6-bromo-4-nitro-1-oxo-isoindolin-2-yl) piperidine-2,6-dione

To a solution of methyl 5-bromo-2-(bromomethyl)-3-nitro-benzoate (29.76 g, 50.59 mmol, 60% purity) and 3-aminopiperidine-2,6-dione (9.99 g, 60.71 mmol) in acetonitrile (290 mL) was added $K_2CO_3$ (17.48 g, 126.47 mmol). The suspension was stirred at 50° C. for 12 hr. The reaction was filtered, and the filter cake was further washed thoroughly with acetonitrile (100 mL) and water (200 mL) to afford a gray residue. The residue was dried under vacuum to afford the title compound (10.82 g, 29.39 mmol, 58% yield) as a gray solid, which was used without further purification. $^1H$ NMR (400 MHz, DMSO-$d_6$) δ=11.07-11.03 (m, 1H), 8.60 (d, J=1.8 Hz, 1H), 8.38-8.35 (m, 1H), 5.18 (dd, J=5.1, 13.0 Hz, 1H), 4.90-4.74 (m, 2H), 2.96-2.86 (m, 1H), 2.55 (br d, J=4.3 Hz, 2H), 2.09-1.95 (m, 1H).

Synthesis of 3-(4-amino-6-bromo-1-oxo-isoindolin-2-yl) piperidine-2,6-dione

To a solution of 3-(6-bromo-4-nitro-1-oxo-isoindolin-2-yl) piperidine-2,6-dione (3.60 g, 9.78 mmol) in AcOH (42 mL) was added portion-wise iron powder (2.73 g, 48.89 mmol). The mixture was stirred at 50° C. for two hr. The reaction was filtered and the solid was washed by DMF (3×100 mL). The filter cake was dried under reduced pressure to afford the title compound (1.11 g, crude) as a white solid that was used without further purifications. MS ($M+H^+$): 338.21.

Synthesis of tert-butyl N-[6-bromo-2-(2,6-dioxo-3-piperidyl)-1-oxo-isoindolin-4-yl]carbamate To a solution of 3-(4-amino-6-bromo-1-oxo-isoindolin-2-yl) piperidine-2,6-dione (1.89 g, 5.59 mmol) in DMF (38 mL) were added di-tert-butyl dicarbonate ($Boc_2O$, 2.56 g, 11.74 mmol), N,N-diisopropylethylamine (2.89 g, 22.36 mmol) and 4-dimethylaminopyridine (DMAP, 819 mg, 6.71 mmol). The mixture was stirred at 120° C. for 2 hr. After completion of the reaction, it was poured into $H_2O$ (50 mL), and extracted with EtOAc (3×50 mL). The combined organic layers were washed with brine (2×50 mL), dried over $Na_2SO_4$, filtered and concentrated under reduced pressure to give a sticky residue. To the residue was added EtOAc/petroleum ether (60 mL, 5/1), and a white solid formed. The solid was collected by filtration and washed by petroleum ether (2×20 mL). The filter cake was dried under reduced pressure to afford the title compound (450 mg, 18% yield) as a white solid. MS ($M+H^+$): 438.21.

Synthesis of tert-butyl N-[2-(2,6-dioxo-3-piperidyl)-1-oxo-6-(4,4,5,5-tetramethyl-1,3,2-dioxaborolan-2-yl) isoindolin-4-yl] carbamate To a solution of tert-butyl N-[6-bromo-2-(2,6-dioxo-3-piperidyl)-1-oxo-isoindolin-4-yl] carbamate (450 mg, 1.03 mmol) in dioxane (20 mL) were added potassium acetate (151 mg, 1.54 mmol), Pd(dppf)$Cl_2$ (75 mg, 0.10 mmol) and pinacol diborane (782 mg, 3.08 mmol). The mixture was stirred at 100° C. for 4 hr. After completion of the reaction, 30 mL of EtOAc/petroleum ether (10/1) were added, and a solid was formed. The solid was collected by filtration and washed by petroleum ether (2×20 mL). The cake was dried under reduced pressure to afford the title compound (430 mg, crude) as a white solid that was used without further purification. $^1H$ NMR (400 MHz, DMSO-$d_6$) δ=11.02 (s, 1H), 9.23 (s, 1H), 8.13 (s, 1H), 7.68 (s, 1H), 5.16-5.07 (m, 1H), 4.56-4.32 (m, 2H), 2.96-2.86 (m, 1H), 2.62 (br d, J=18.1 Hz, 1H), 2.42-2.35 (m, 1H), 1.49 (s, 9H), 1.32 (s, 12H).

Synthesis of tert-butyl N-[2-(2,6-dioxo-3-piperidyl)-6-hydroxy-1-oxo-isoindolin-4-yl]carbamate To a solution of tert-butyl N-[2-(2,6-dioxo-3-piperidyl)-1-oxo-6-(4,4,5,5-tetramethyl-1,3,2-dioxaborolan-2-yl) isoindolin-4-yl] carbamate (430 mg, 0.89 mmol) in THF (8 mL) and $H_2O$ (4 mL) was added sodium perborate (464 mg, 3.01 mmol). The mixture was stirred at 20° C. for 12 hr. The reaction was then poured into $H_2O$ (20 mL), and extracted with EtOAc (3×20 mL). The combined organic layers were washed with brine (2×20 mL), dried over $Na_2SO_4$, filtered and concentrated under reduced pressure to give a residue. To the residue was added 100 mL of EtOAc/petroleum ether (1/4), and a white solid was formed. The solid was collected by filtration and washed by petroleum ether (2×20 mL). The filter cake was dried under reduced pressure to afford the title compound (130 mg, 39% yield) as a white solid that was used without further purification. MS (M+H$^+$): 376.23.

Synthesis of tert-butyl N-[2-(2,6-dioxo-3-piperidyl)-6-fluorosulfonyloxy-1-oxo-isoindolin-4-yl] carbamate To a solution of tert-butyl N-[2-(2,6-dioxo-3-piperidyl)-6-hydroxy-1-oxo-isoindolin-4-yl] carbamate (130 mg, 0.35 mmol) and N-(4-acetamidophenyl)-N-fluorosulfonyl-sulfamoyl fluoride (109 mg, 0.35 mmol) in THF (7.5 mL) was added 1,8-diazabicyclo[5.4.0]undec-7-ene (53 mg, 0.35 mmol). The mixture was stirred at 20° C. for one hr. After completion of the reaction, it was concentrated under reduced pressure to afford the crude title compound (130 mg) as a brown solid that was used without further purification.

Synthesis of 4-amino-2-(2,6-dioxo-3-piperidyl)-6-fluorosulfonyloxy-1-oxo-isoindoline (10)

10

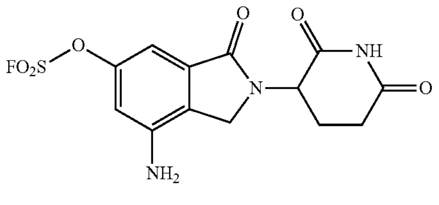

To a solution of tert-butyl N-[2-(2,6-dioxo-3-piperidyl)-6-fluorosulfonyloxy-1-oxo-isoindolin-4-yl] carbamate (20 mg, 0.04 mmol) in DCM (0.5 mL) was added trifluoroacetic acid (154 mg, 1.35 mmol). The mixture was stirred at 0° C. for two hr. After completion of the reaction, the reaction mixture was concentrated under reduced pressure to give a residue. The residue was purified by prep-HPLC to afford the title compound (1.3 mg, 0.003 mmol, 8% yield) as a white solid. MS (M+H$^+$): 358.0, $^1$H NMR (400 MHz, DMSO-$d_6$) δ=11.04 (s, 1H), 7.01-6.95 (m, 1H), 6.88 (d, J=1.9 Hz, 1H), 5.18-5.08 (m, 1H), 4.32-4.10 (m, 2H), 2.98-2.85 (m, 1H), 2.72-2.57 (m, 1H), 2.36 (br s, 1H), 2.10-1.99 (m, 1H).

Example 12; Synthesis of 3-(6-((4-methyl-1H-pyrazol-1-yl)sulfonyl)-1-oxoisoindolin-2-yl)piperidine-2,6-dione (11)

11

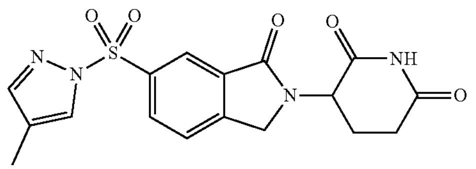

The title compound was prepared from 2-(2,6-dioxo-3-piperidyl)-3-oxo-isoindoline-5-sulfonyl chloride and 4-methyl-1H-pyrazole using the method described in Example 8. MS (M+W): 389.1. $^1$H NMR (400 MHz, DMSO-$d_6$) δ=11.02 (s, 1H), 8.31-8.29 (m, 1H), 8.19 (dd, J=1.8, 8.1 Hz, 1H), 8.15-8.12 (m, 1H), 7.93-7.88 (m, 1H), 7.76 (s, 1H), 5.18-5.09 (m, 1H), 4.64-4.55 (m, 1H), 4.51-4.42 (m, 1H), 2.96-2.83 (m, 1H), 2.65-2.55 (m, 1H), 2.46-2.31 (m, 1H), 2.06-1.97 (m, 4H).

Example 13: Synthesis of 3-(6-((4-fluoro-1H-pyrazol-1-yl)sulfonyl)-1-oxoisoindolin-2-yl)piperidine-2,6-dione (12)

12

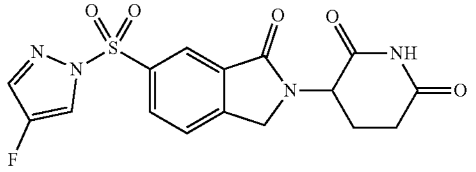

The title compound was prepared from 2-(2,6-dioxo-3-piperidyl)-3-oxo-isoindoline-5-sulfonyl chloride and 4-fluoro-1H-pyrazole using the method described in Example 8. MS (M+H$^+$); 393.1.1H NMR (400 MHz, DMSO-$d_6$) δ=11.09 (br s, 1H), 8.89 (d, J=4.6 Hz, 1H), 8.33-8.25 (m, 2H), 8.17 (d, J=4.3 Hz, 1H), 8.01 (d, J=8.1 Hz, 1H), 5.28-5.15 (m, 1H), 4.71-4.50 (m, 2H), 3.03-2.91 (m, 1H), 2.69-2.64 (m, 1H), 2.52-2.37 (m, 1H), 2.15-2.01 (m, 1H).

Example 14: 3-(1-oxo-6-((4-(trifluoromethyl)-1H-pyrazol-1-yl)sulfonyl)isoindolin-2-yl)piperidine-2,6-dione (13)

13

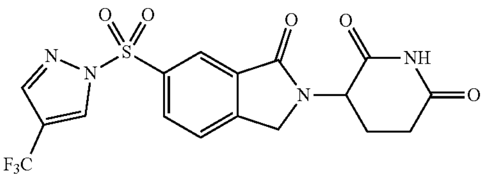

The title compound was prepared from 2-(2,6-dioxo-3-piperidyl)-3-oxo-isoindoline-5-sulfonyl chloride and 4-(trifluoromethyl)-1H-pyrazole using the method described in Example 8. MS (M+H$^+$): 443.1. $^1$H NMR (400 MHz, DMSO-$d_6$) δ=11.04 (s, 1H), 9.38 (s, 1H), 8.45-8.27 (m, 3H), 8.04-7.94 (m, 1H), 5.16 (dd, J=5.1, 13.3 Hz, 1H), 4.71-4.44 (m, 2H), 2.98-2.85 (m, 1H), 2.64-2.58 (m, 1H), 2.47-2.34 (m, 1H), 2.07-1.98 (m, 1H).

Example 15: Synthesis of 3-(1-oxo-6-((4-(trifluoromethyl)-1H-imidazol-1-yl)sulfonyl)isoindolin-2-yl)piperidine-2,6-dione (14)

14

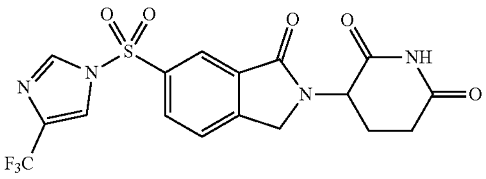

The title compound was prepared from 2-(2,6-dioxo-3-piperidyl)-3-oxo-isoindoline-5-sulfonyl chloride and 4-(trifluoromethyl)-1H-imidazole using the method described in Example 8. MS (M+H$^+$): 443.1. $^1$H NMR (400 MHz, DMSO-$d_6$) δ=11.03 (s, 1H) 8.69-8.78 (m, 2H) 8.53 (d, J=1.50 Hz, 1H) 8.43 (dd, J=8.13, 1.88 Hz, 1H) 8.00 (d, J=8.13 Hz, 1H) 5.17 (dd, J=13.26, 5.00 Hz, 1H) 4.59-4.68 (m, 1H) 4.46-4.55 (m, 1H) 2.85-2.98 (m, 1H) 2.56-2.65 (m, 1H) 2.34-2.47 (m, 1H) 1.97-2.05 (m, 1H).

Example 16: Synthesis of 3-(6-((3-fluoro-1H-pyrazol-1-yl)sulfonyl)-1-oxoisoindolin-2-yl)piperidine-2,6-dione (15)

15

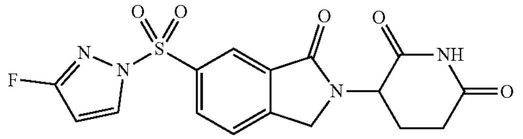

The title compound was prepared from 2-(2,6-dioxo-3-piperidyl)-3-oxo-isoindoline-5-sulfonyl chloride and 3-fluoro-1H-pyrazole using the method described in Example 8. MS (M+H$^+$): 393.1. $^1$H NMR (400 MHz, DMSO-$d_6$) δ=11.03 (s, 1H) 8.61 (t, J=2.88 Hz, 1H) 8.19-8.28 (m, 2H) 7.95 (d, J=8.13 Hz, 1H) 6.56 (dd, J=5.75, 3.00 Hz, 1H) 5.15 (dd, J=13.32, 5.07 Hz, 1H) 4.58-4.66 (m, 1H) 4.45-4.54 (m, 1H) 2.85-2.94 (m, 1H) 2.60-2.65 (m, 1H) 2.36-2.45 (m, 1H) 1.99-2.06 (m, 1H).

Example 17: Synthesis of 3-(6-((4-methyl-1H-pyrazol-1-yl)sulfonyl)-1-oxoisoindolin-2-yl)piperidine-2,6-dione (16)

16

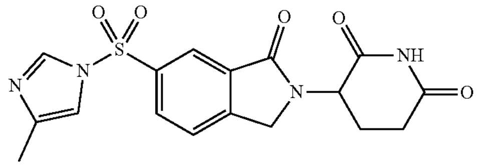

The title compound was prepared from 2-(2,6-dioxo-3-piperidyl)-3-oxo-isoindoline-5-sulfonyl chloride and 4-methyl-1H-imidazole using the method described in Example 8. MS (M+H$^+$): 387.0. $^1$H NMR (400 MHz, DMSO-$d_6$) δ=14.27-13.76 (m, 2H), 11.00 (s, 1H), 8.94 (d, J=1.1 Hz, 1H), 7.92-7.82 (m, 2H), 7.57 (d, J=7.9 Hz, 1H), 7.39 (s, 1H), 5.12 (dd, J=5.1, 13.3 Hz, 1H), 4.54-4.28 (m, 2H), 2.99-2.84 (m, 1H), 2.60 (br d, J=17.4 Hz, 1H), 2.48-2.33 (m, 1H), 2.28 (s, 3H), 2.12-1.89 (m, 1H).

Example 18: Synthesis of 3-(6-((4-fluoro-1H-imidazol-1-yl)sulfonyl)-1-oxoisoindolin-2-yl)piperidine-2,6-dione (17)

17

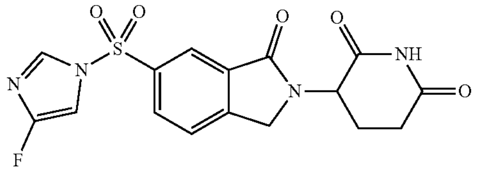

The title compound was prepared from 2-(2,6-dioxo-3-piperidyl)-3-oxo-isoindoline-5-sulfonyl chloride and 4-fluoro-1H-imidazole using the method described in Example 8. MS (M+H$^+$): 393.1. $^1$H NMR (400 MHz, DMSO-$d_6$) δ=11.04 (s, 1H), 8.43 (d, J=1.6 Hz, 1H), 8.39-8.33 (m, 2H), 7.99 (d, J=8.1 Hz, 1H), 7.80 (dd, J=1.8, 8.1 Hz, 1H), 5.17 (dd, J=5.1, 13.3 Hz, 1H), 4.69-4.44 (m, 2H), 3.00-2.83 (m, 1H), 2.65-2.57 (m, 1H), 2.46-2.31 (m, 1H), 2.07-1.94 (m, 1H).

Example 19: Synthesis of 3-(1-oxo-6-((3-(trifluoromethyl)-1H-pyrazol-1-yl)sulfonyl)isoindolin-2-yl) piperidine-2,6-dione (18)

18

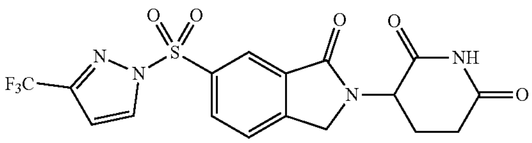

Synthesis of 3-(6-benzylsulfanyl-1-oxo-isoindolin-2-yl)piperidine-2,6-dione

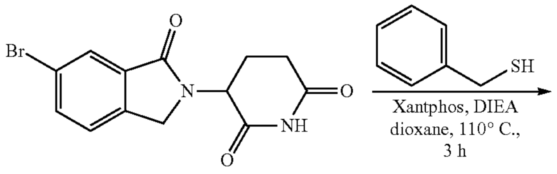

-continued

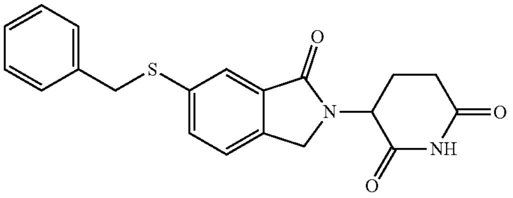

A mixture of 3-(6-bromo-1-oxo-isoindolin-2-yl)piperidine-2,6-dione (5 g, 15.47 mmol, 1 eq), phenylmethanethiol (2.50 g, 20.12 mmol, 2.36 mL, 1.3 eq), $Pd_2(dba)_3$ (708.45 mg, 773.65 μmol, 0.05 eq), DIEA (4.00 g, 30.95 mmol, 5.39 mL, 2 eq) and Xantphos (895.30 mg, 1.55 mmol, 0.1 eq) in dioxane (50 mL) was degassed and purged 3 times with $N_2$, and then the mixture was stirred at 110° C. for 3 h under $N_2$ atmosphere. The reaction liquid was filtered, and the solid was collected and dried over reduced pressure to afford the title compound (6 g crude) as a yellow solid.

Synthesis of 2-(2,6-dioxo-3-piperidyl)-3-oxo-isoindoline-5-sulfonyl chloride

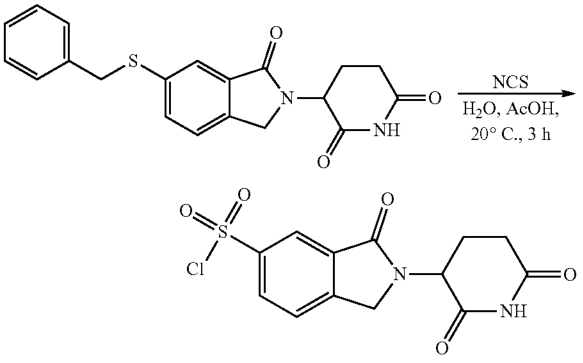

To a solution of 3-(6-benzylsulfanyl-1-oxo-isoindolin-2-yl)piperidine-2,6-dione (2 g, 5.46 mmol, 1 eq) in $H_2O$ (2 mL) and acetic acid (16 mL) was added NCS (1.46 g, 10.92 mmol, 2 eq). The mixture was stirred at 20° C. for 2 h. The reaction liquid was filtered, and the solid was collected to afford the title compound (1.7 g crude) as a white solid.

Synthesis of 3-[1-oxo-6-[3-(trifluoromethyl)pyrazol-1-yl]sulfonyl-isoindolin-2-yl]piperidine-2,6-dione (18)

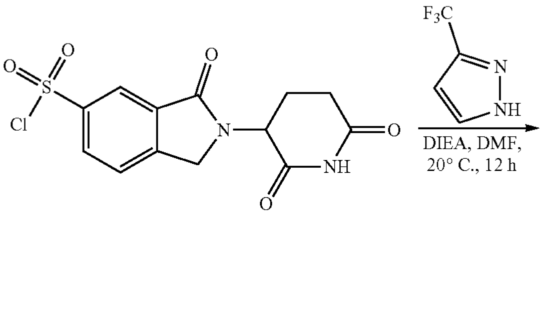

-continued

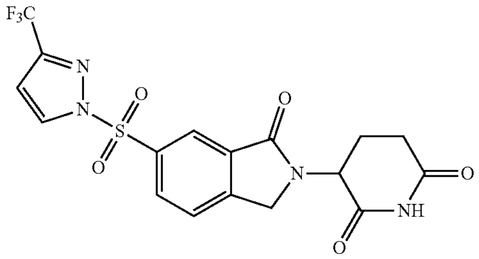

18

To a solution of 2-(2,6-dioxo-3-piperidyl)-3-oxo-isoindoline-5-sulfonyl chloride (80 mg, 233.40 μmol, 1 eq) in DMF (2 mL) was added DIEA (60.33 mg, 466.81 μmol, 81.31 μL, 2 eq) and 3-(trifluoromethyl)-1H-pyrazole (31.76 mg, 233.40 μmol, 1 eq). The mixture was stirred at 20° C. for 12 h. The reaction mixture was purified by prep-HPLC (FA condition column: Phenomenex Luna 80*30 mm*3 μm; mobile phase: [water(FA)-$CH_3CN$]; B %: 25%-55%, 8 min) to afford the title compound (42 mg, 94.94 μmol, 40.68% yield, 99.79% purity) as a white solid. $^1H$ NMR (400 MHz, DMSO-$d_6$) δ=11.03 (s, 1H) 8.91 (dd, J=2.75, 0.88 Hz, 1H) 8.30-8.38 (m, 2H) 7.99 (d, J=8.13 Hz, 1H) 7.16 (d, J=2.75 Hz, 1H) 5.15 (dd, J=13.32, 5.07 Hz, 1H) 4.46-4.68 (m, 2H) 2.84-2.97 (m, 1H) 2.56-2.65 (m, 1H) 2.40 (qd, J=13.17, 4.38 Hz, 1H) 1.96-2.05 (m, 1H). MS: $(M+H^+)$: 443.1; F NMR (400 MHz, DMSO-$d_6$) δ=−61.739.

Example 20: Synthesis of 1-((2-(2,6-dioxopiperidin-3-yl)-3-oxoisoindolin-5-yl)sulfonyl)-5-methylpyrimidine-2,4(1H,3H)-dione (19)

19

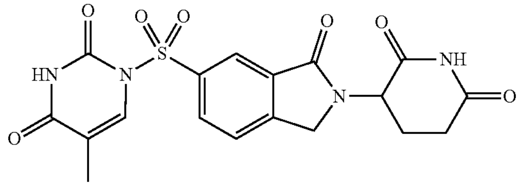

The title compound was prepared from 2-(2,6-dioxo-3-piperidyl)-3-oxo-isoindoline-5-sulfonyl chloride and 5-methyl-1H-pyrimidine-2,4-dione using the method described in Example 8. MS $(M+H^+)$: 433.1. $^1H$ NMR (400 MHz, DMSO-$d_6$) δ=11.23-12.41 (m, 1H) 11.03 (br s, 1H) 8.23-8.34 (m, 2H) 8.07 (d, J=1.25 Hz, 1H) 7.93 (d, J=8.00 Hz, 1H) 5.16 (dd, J=13.26, 5.13 Hz, 1H) 4.45-4.69 (m, 2H) 2.84-2.99 (m, 1H) 2.57-2.65 (m, 1H) 2.35-2.46 (m, 1H) 1.99-2.06 (m, 1H) 1.82-1.91 (m, 3H).

Example 21: Synthesis of 5-amino-1-((2-(2,6-dioxopiperidin-3-yl)-3-oxoisoindolin-5-yl)sulfonyl) pyrimidine-2,4(1H,3H)-dione (20)

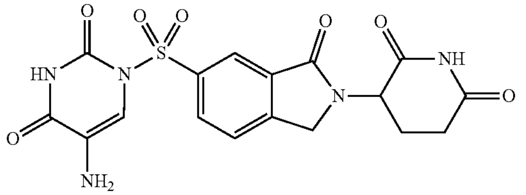

20

The title compound was prepared from 2-(2,6-dioxo-3-piperidyl)-3-oxo-isoindoline-5-sulfonyl chloride and 4-amino-1H-pyrimidin-2-one using the method described in Example 8. MS ($M+H^+$); 418.1. $^1H$ NMR (400 MHz, DMSO-$d_6$) δ=11.04 (s, 1H) 8.23-8.27 (m, 2H) 8.18 (d, J=7.88 Hz, 1H) 7.88-8.01 (m, 3H) 6.00 (d, J=7.88 Hz, 1H) 5.18 (dd, J=13.32, 5.07 Hz, 1H) 4.46-4.68 (m, 2H) 2.87-2.98 (m, 1H) 2.58-2.67 (m, 1H) 2.43 (br dd, J=12.88, 4.38 Hz, 1H) 1.98-2.10 (m, 1H).

Example 22: Synthesis of 1-((2-(2,6-dioxopiperidin-3-yl)-3-oxoisoindolin-5-yl)sulfonyl)pyrimidine-2,4 (1H,3H)-dione (21)

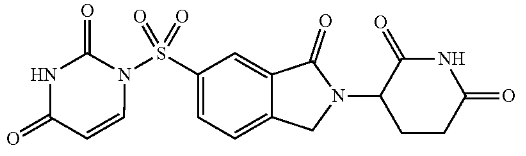

21

The title compound was prepared from 2-(2,6-dioxo-3-piperidyl)-3-oxo-isoindoline-5-sulfonyl chloride and 1H-pyrimidine-2,4-dione using the method described in Example 8. MS (M+H): 419.1. $^1H$ NMR (400 MHz, DMSO-$d_6$) δ=11.86-11.64 (m, 1H), 11.03 (s, 1H), 8.34-8.27 (m, 2H), 8.18 (d, J=8.4 Hz, 1H), 7.95 (d, J=8.0 Hz, 1H), 5.86 (d, J=8.4 Hz, 1H), 5.17 (dd, J=5.0, 13.3 Hz, 1H), 4.69-4.45 (m, 2H), 2.99-2.85 (m, 1H), 2.66-2.57 (m, 1H), 2.45-2.35 (m, 1H), 2.09-1.98 (m, 1H).

Example 23: Cellular CRBN NanoBret Engagement Assay

To assess CRBN binding in cells, a Nano-bioluminescence resonance energy transfer (NanoBRET™) assay was developed that measures the dose-dependent reduction in BRET signal following displacement of a fluorescent CRBN tracer from NanoLuc-tagged CRBN, similar to a recently reported assay that used transient transfection (Vasta et al., Methods Mol Biol. 2365:265-282 (2021)). The previously developed BODIPY-lenalidomide probe (Wang et al., Nat Chem Biol. 17:711-717 (2021)) was found to be cell permeable and resulted in efficient NanoBRET™ signal measured by a custom designed 450-80/520 BRET module (BMG Labtech).

HEK293T cells were transduced with lentivirus and put under puromycin selection (5 μg/mL) for two weeks to produce a cell line stably expressing CRBN with N-terminally fused NanoLuc® luciferase (NanoLuc-CRBN). After antibiotic selection, cells were cultured in DMEM (Gibco, Life Technologies) supplemented with 10% FBS and 1 μg/mL puromycin to maintain stable NanoLuc®-CRBN expression. To run the assay, cells were cultured to confluency in 10 $cm^2$ tissue culture treated plates (Corning, 430165), washed with PBS and trypsinized at room temperature to detach from the cell culture plate. After 3-4 min, the trypsin was quenched with 5× volume DMEM media (Gibco, Life Technologies) with 10% FBS and cells were collected by centrifugation (1000 rpm, 5 min). The supernatant was removed by vacuum aspiration and the pellet was then resuspended in Opti-MEM™ without phenol red. The density of this cell suspension was determined by diluting the cells 1:1 with trypan blue, then counting using a Countess II (Thermo Fischer Scientific) and then diluted to the required volume at $2\times10^5$ viable cells/mL in Opti-MEM™ I (Gibco, Life Technologies). To this suspension was added the CRBN engagement tracer (stock at 10 μM in 31.25% PEG-400, 12.5 mM HEPES, pH 7.5, filtered using a 0.22 μm nitrocellulose membrane; final concentration in cell suspension for assay at 250 nM). Cells were then plated in a white/opaque cell culture treated 384-well plate (Corning, 3570) at volume of 50 μL/well. After plating, the assay plate was centrifuged (500×g, 5 min) and covered in aluminum foil. Compounds for testing were added to the plate using a D300e Digital Dispenser (HP) in duplicate 12-pt titrations from a 10 mM stock in DMSO, with DMSO normalized to 1% total volume. The plate was then placed in an incubator at 37° C., 5% $CO_2$ for two hours. After incubation, the plate was removed and set on the bench to cool to room temperature (~10-15 min). The NanoLuc® substrate (500× solution) and extracellular inhibitor (1500× solution) were diluted in Opti-MEM™ I (Gibco, Life Technologies) to prepare a 3× solution. This was then added to each well (25 μL/well). The plate was read on a Pherastar FSX microplate reader with simultaneous dual emission capabilities to read 384-well plates at 450 and 520 nm. The NanoBRET™ ratio was calculated by dividing the signal at 520 nm by the signal at 450 nm for each sample. Duplicate points were averaged and plotted against [compound, M] to generate an $EC_{50}$ curve. The NanoLuc® substrate and extracellular inhibitor were purchased as a kit from Promega Corporation and used as is from the box—Promega NanoBRET™ Nano-Glo® Substrate/Inhibitor; Promega Catalog number N2161 for 10,000 assay kit.

TABLE 1

Cellular CRBN NanoBret Engagement Assay Results

| Compound | CRBN NanoBRET ™ $IC_{50}$ (nM) |
|---|---|
| 1 | 256 |
| 2 | 3451 |
| 3 | 0.88 |
| 4 | 72 |
| 5 | 12640 |
| 6 | 540 |
| 7 | 21 |
| 8 | 78 |
| 9 | 310 |
| 10 | 890 |
| 11 | 3752 |
| 12 | 2341 |
| 13 | 43.6 |
| 14 | 54.9 |
| 15 | 1629 |

TABLE 1-continued

Cellular CRBN NanoBret Engagement Assay Results

| Compound | CRBN NanoBRET ™ $IC_{50}$ (nM) |
|---|---|
| 16 | 454 |
| 17 | 324 |
| 18 | 50.4 |
| 19 | 1377 |
| 20 | 8630 |
| 21 | 4298 |

Example 24: Compound 1 Downregulates WDYHV1

FIG. 1 shows the relative fold-change (FC) abundance of proteins in MOLT4 cells treated with 1 μM compound 1 for 5 hours determined using mass spectrometry proteomics (protocol was published previously: Donovan et al. Cell/83: 1714-1731 (2020)). N-terminal glutamine amidohydrolase (NTAQ1 or WDYHV1) was clearly downregulated. Further confirmation was achieved in THP1 cells. The activity of cullin ring ligases (CRLs) has been shown to be reliant upon neddylation, and the NEDD8-activating enzyme (NAE) inhibitor MLN4924 is often used as confirmatory evidence that degradation is mediated by CRLs, including the CRBN E3 ubiquitin ligase complex $CRL4^{CRBN}$ (Deshales et al., Subcell Biochem 54:41-56 (2010); Soucy et al., Nature 58:732-36 (2009)). Pre-treatment of cells with MLN4924 rescued downregulation of NTAQ1 by Compound 1, showing that degradation required the active CRL.

Figure 2:
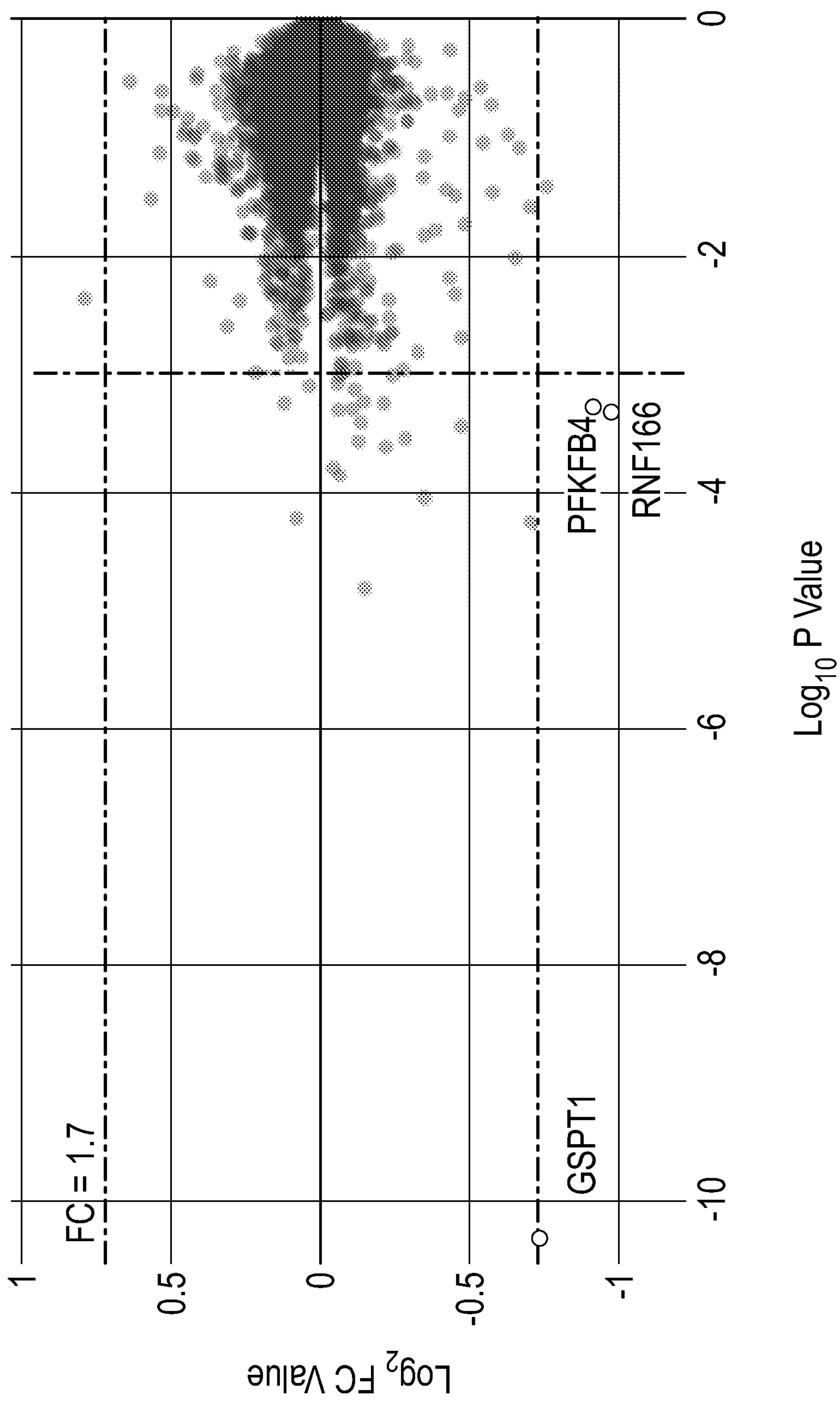
FIG. 2 is a graph of $Log_2$ FC value versus $Log_{10}$ P value showing relative FC abundance of proteins in MOLT4 cells treated with 1 μM compound 4 showing that GSPT1, PFKFB4 and RNF166 were downregulated.

FIG. 2 shows the relative FC abundance of proteins in MOLT4 cells treated with 1 μM compound 4 for 5 hours determined using mass spectrometry proteomics (protocol was published previously: Donovan et al., Cell 183:1714-31 (2020). GSPT1, PFKFB4 and RNF166 were clearly downregulated.

Example 25: Mass Spec Data Confirming Cereblon Labeling and Peptide Mapping

The hsCRBN-DDB1 complex was treated with DMSO or an equimolar concentration of compound 1 for 24 hr at room temperature before being analyzed by LC-MS using an HPLC system (Shimadzu, Marlborough, MA) interfaced to an LTQ ion trap mass spectrometer (ThermoFisher Scientific, San Jose, CA). After injecting 5 μg, proteins were desalted for four min on column with 100% A and then eluted with an HPLC gradient (0-100% B in 1 min; A=0.2 M acetic acid in water; B=0.2 M acetic acid in acetonitrile). The mass spectrometer was programmed to acquire full scan mass spectra (m/z 300-2000) in profile mode (spray voltage=4.5 kV). Mass spectra were deconvoluted using MagTran software version 1.03b2.

To identify the site of covalent modification, compound 1-treated hsCRBN-DDB1 complex was reduced with 10 mM dithiothreitol for 30 min at 56° C., alkylated with 25 mM 4-vinyl pyridine for 30 min at room temperature, and digested with trypsin (Promega, Madison, WI) overnight at 37° C. Peptides were desalted using C18 (SOLA™, ThermoFisher Scientific, Madison, WI), dried by vacuum centrifugation, reconstituted in 50% acetonitrile, 1% formic acid, 100 mM ammonium acetate, and analyzed by CE-MS using a ZipChip CE-MS instrument and autosampler (908 devices, Boston, MA) interfaced to a QExactive HF mass spectrometer (ThermoFisher Scientific). Peptides were resolved at 500 V/cm using an HR chip with a background electrolyte consisting of 50% acetonitrile with 1% formic acid. The mass spectrometer was operated in data dependent mode and the five most abundant ions in each MS scan (m/z 300-2000, 60K resolution, 3E6 target, 100 ms max fill time) were subjected to MS/MS (15K resolution, 1E5 target, 100 ms max fill time). Dynamic exclusion was enabled with a repeat count of 1 and an exclusion duration of five s. Raw mass spectrometry data files were converted to .mgf using Multiplierz software and searched against a custom database containing the hsCRBN-DDB1 sequences using Mascot version 2.6.2. Search parameters specified fixed vinylpyridine modification of cysteine, variable methionine oxidation, and variable modification of cysteine. Modified spectra were examined and figures prepared using mzStudio software.

Figure 3A:
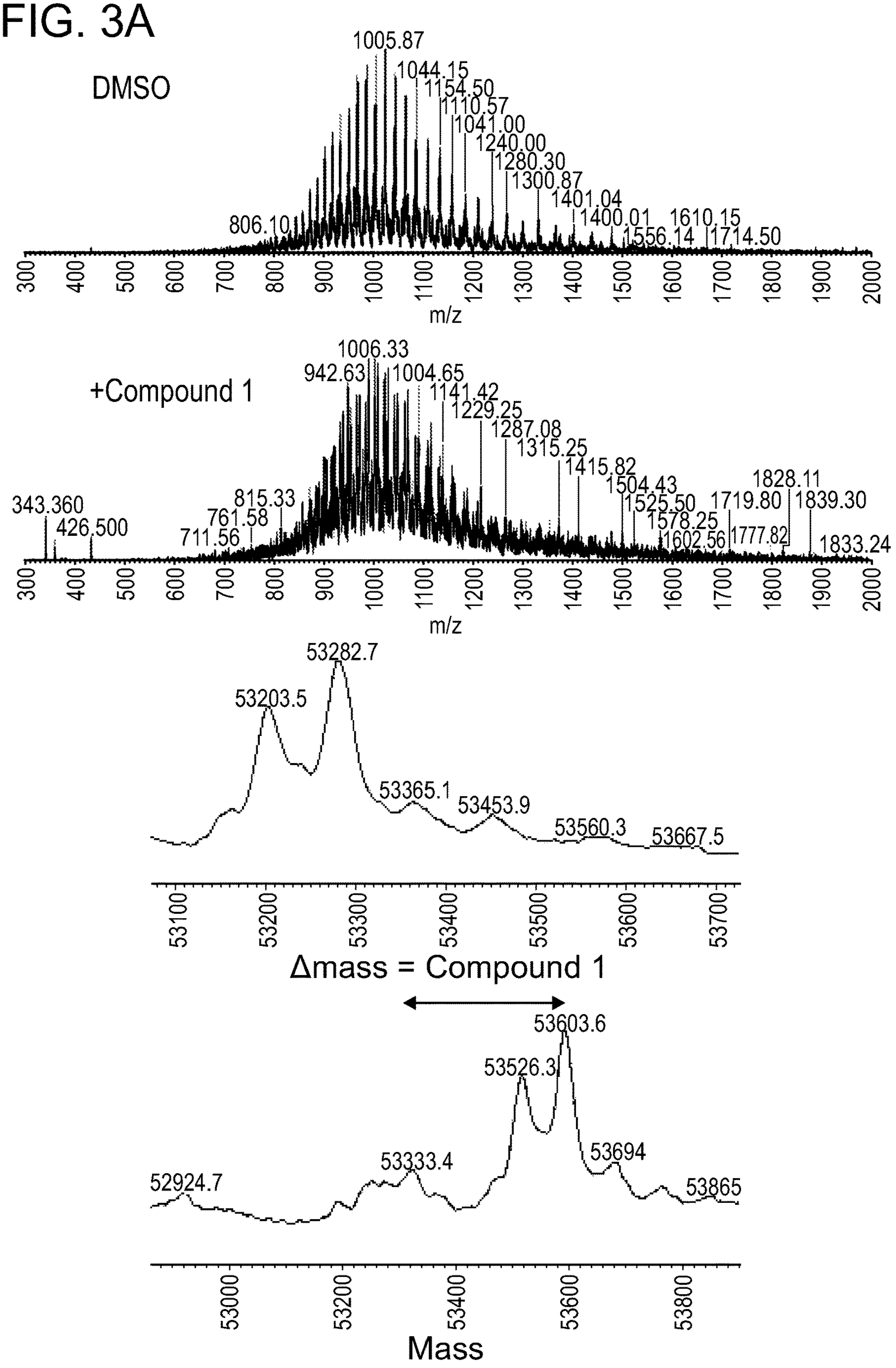
FIG. 3A and FIG. 3B show that cereblon is exclusively labeled at His353 by compound 1.
Figure 3B:
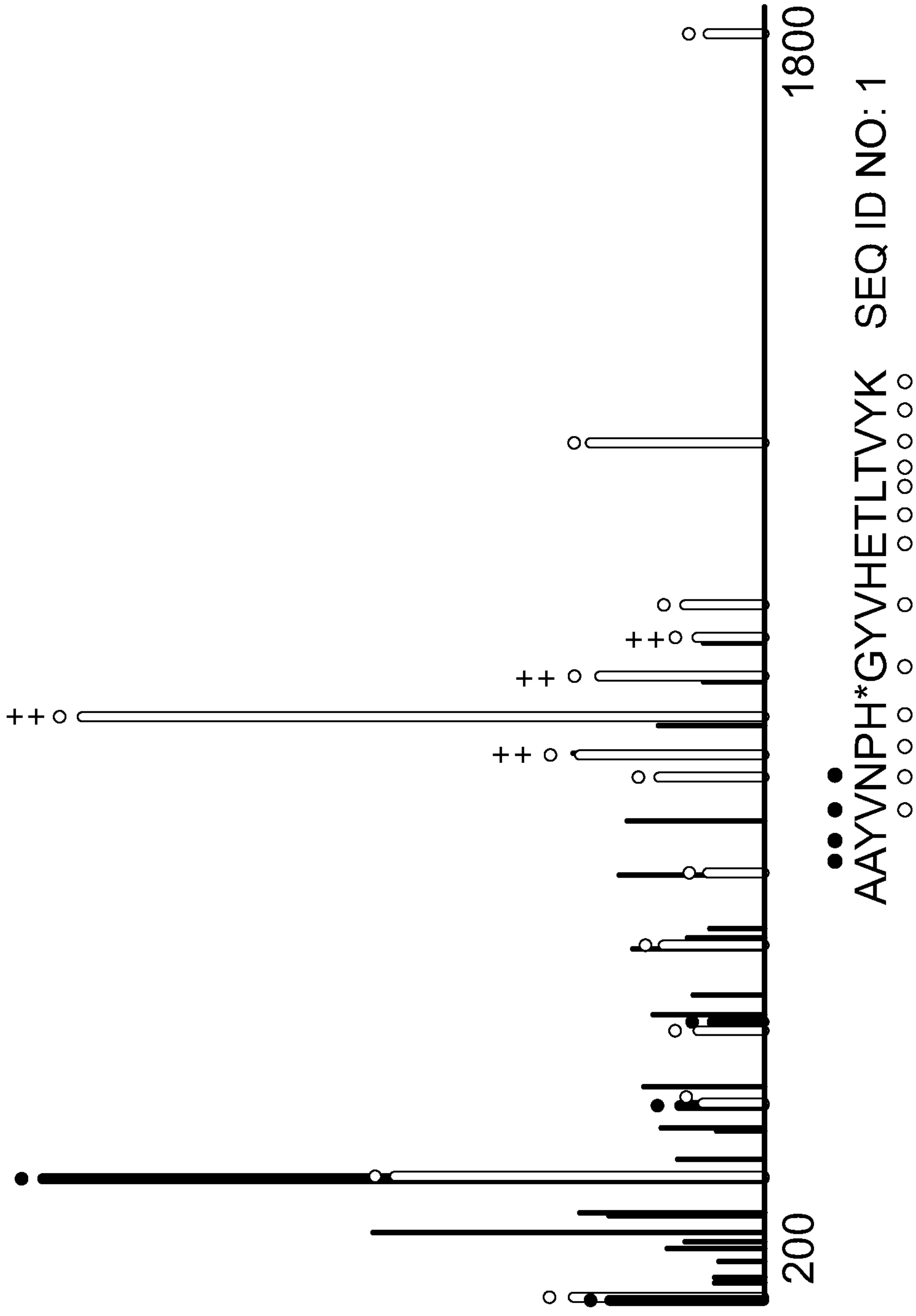

As shown in FIG. 3, cereblon is exclusively labeled at His353 by compound 1. FIG. 3A shows the mass spectra (left) and zero-charge mass spectra (right) of the CRBN-DDB1 complex treated with DMSO (top) or an equimolar concentration of compound 1 for 24 hr at room temperature (bottom). CRBN exhibits an increase in mass consistent with modification by a single molecule of compound 1. FIG. 3B shows the MS/MS spectrum of CRBN peptide $^{347}$AAYVNPH*GYVHETLTVYK$^{364}$ [SEQ ID NO: 1] modified with compound 1 indicating covalent labeling of His353. Ions of type b and y are indicated with blue or red glyphs, respectively. H*, compound 1 modified residue. ++, doubly charged product ion.

Figure 3C:
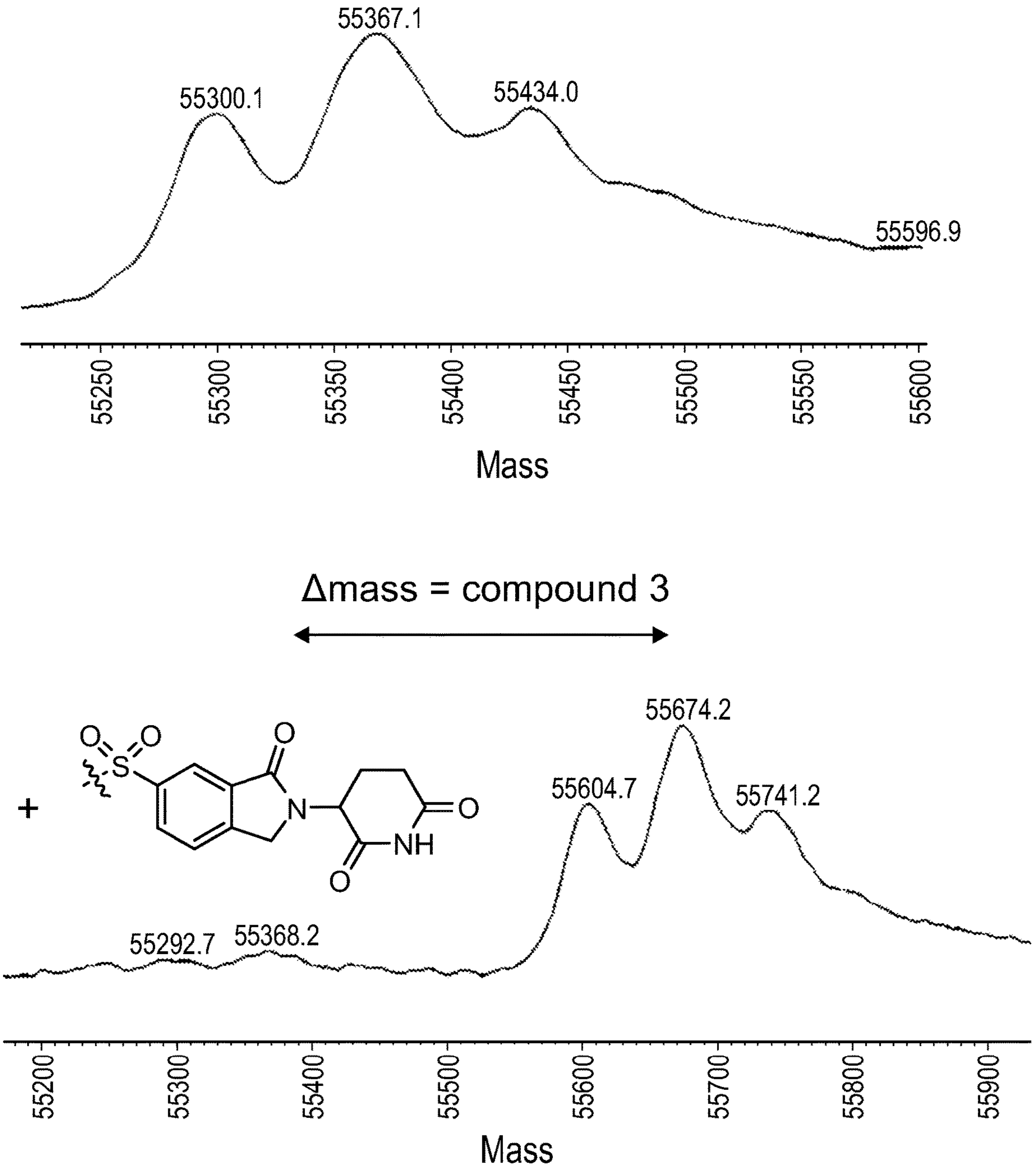
FIG. 3C is a set of two partial MS traces showing the intact MS of CRBN/DDB1 (molecular weight trace of CRBN shown) and the mass shift of CRBN following treatment with 1 eq. Compound 3 (4 hours), which is commensurate with sulfonylation (Δmass=307).

Compounds 2, 3, 4, and 7 were shown to form an adduct with CRBN using the same MS assay. For example, FIG. 3C shows the intact MS of CRBN/DB1 (molecular weight trace of CRBN shown) and the mass shift of CRBN following treatment with 1 eq. of compound 3 (4 hr), which is commensurate with sulfonylation (Δmass=307). Compounds 4 and 7 were also shown to label His353 using the same peptide mapping assay.

Example 26. Inhibition of IKZF1 Degradation by Lenalidomide Using Compound 3

Experiments were carried out in a 6-well plate (Corning). $2\times10^6$ MOLT4 cells were dispensed into three wells in a total volume of 1.5 mL per well. The DMSO-treated sample was initially treated with 1.5 μL DMSO. The lenalidomide only-treated sample was initially treated with 1.5 μL of DMSO (to balance overall DMSO content). The compound 3-treated sample was treated with 1.5 μL of 1 mM compound 3 for a final concentration of 1 μM. The samples were incubated for 2 hr at 37° C. and 5% $CO_2$. After 2 hr, 1.5 μL of DMSO were added to the DMSO treated sample 1.5 μL of 1 mM lenalidomide were added to the lenalidomide only-treated sample for a final concentration of 1 μM lenalidomide, and 1.5 μL 1 mM compound 3 were added to the compound 3-treated sample for a final concentration of 1 μM compound 3. Cells were incubated at 37° C. and 5% $CO_2$ for 5 hours. After 5 hours, cells were removed from the 6-well plate and transferred to 1.5 mL microcentrifuge tubes. Cells were centrifuged for 5 min at 800×g, the supernatant was removed, and the cells were washed with 1 mL of PBS. Pellets were flash-frozen in liquid nitrogen and left at −80° C. until further use. Cell pellets were lysed in RIPA buffer (Thermo Scientific) supplemented with 1× protease inhibitor cocktail (Roche cOmplete™). Briefly, cell pellets were resuspended in lysis buffer, briefly, vortexed, and incubated on ice for 10 min. After 10 min, lysates were centrifuged on a tabletop centrifuge for 10 min at maximum speed and 4°

Figure 4:
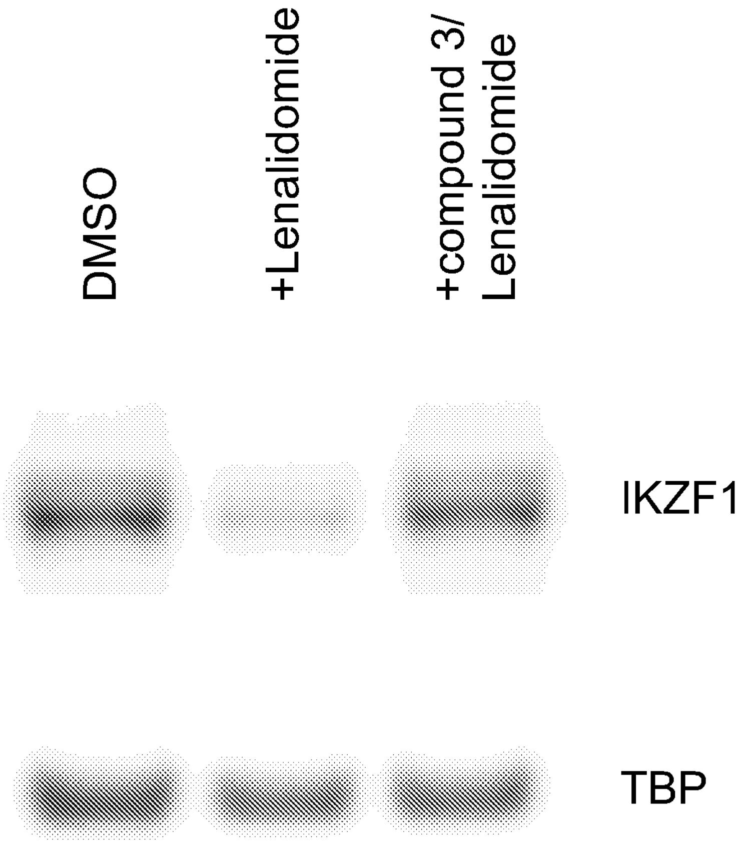
FIG. 4 is a Western blot showing that compound 3 inhibits the degradation of IKZF1 by lenalidomide in MOLT4 cells (2 hours pre-treatment with compound 3 followed by 5 hours incubation with lenalidomide).

C. Supernatants transferred to fresh 1.5 mL Eppendorf tubes and quantified via a BCA assay (Thermo Scientific). Lysates were separated on a Bolt™ 4-12% Bis-Tris Plus mini gel (Invitrogen), and transferred to a 0.2 μm nitrocellulose membrane using a TransBlot Turbo Transfer System from Bio-Rad. After transfer, the membrane was washed briefly with 1×TBS-T and stained with Ponceau to be able to accurately divide the membrane for blotting. Membranes were blocked for 1 hour at room temperature in 10% milk (Lab Scientific bioKEMIX, Inc.) in TBS-T before adding IKZF1 (Cell Signaling Technologies) and TBP (Abcam, loading control) antibodies at dilutions of 1:1000 and 1:2000, respectively. Membranes were incubated overnight at 4° C. The following morning, primary antibodies were discarded, and the membranes were washed 3×5 min with TBS-T, prior to adding secondary antibodies (anti-rabbit (Protein Simple) and anti-mouse (Invitrogen) HRP-conjugates for IKZF1 and TBP respectively) at a dilution of 1:5000 in 10% milk in TBS-T. Membranes were incubated at room temperature for 1 hour prior to discarding secondary antibodies and washing 3×5 min with TBS-T. Membranes were developed using a PicoWest detection kit (Thermo Scientific) and imaged on an Amersham Imager 600 (GE Healthcare). Compound 3 clearly inhibits the degradation of IKZF1 by lenalidomide (FIG. 4). The development of new targeted protein degraders that have been designed to hijack the CRBN E3 ligase complex requires validation of CRBN-dependence to substantiate the molecular mode of degradation. Existing methods that validate CRBN-dependence include the use of PROTAC's directed to CRBN itself, where protein depletion may be slow, or CRBN knockout cell lines, which requires genetic engineering. Technical limitations of these approaches necessitate a simple and rapid pharmacological method of CRBN inhibition that can be used in native cells. Compound 3 satisfies this need by potently blocking the small molecule degrader binding site in CRBN. Increasingly, libraries of degrader molecules are being screened phenotypically to identify starting points for hit elaboration, and simultaneously reveal new therapeutic targets amenable to degradation. Compound 3 augments the CRBN target validation toolkit that will advance targeted protein degradation research.

Example 27: Metabolic Profiling and Human Plasma Half-Life

The stability of compounds was assessed in human plasma, human liver microsomes (HLM) and human hepatocytes (Hhep) using procedures previously published (Kong et al., ACS Med Chem Lett 12:1861-1865 (2021)). Human plasma stability $T_{1/2}$ compound 1: 196 min; compound 3: 7 min; compound 7: 2 min; compound 8: <1 min; compound 11: >289 min; compound 12: 92 min; compound 13: 10 min; compound 14: 6.5 min; compound 15: 115 min; compound 16: 287 min; compound 17: 19 min; compound 18: 14 min; compound 19: 239 min, compound 20: >289 min; compound 21: 163 min. HLM stability $T_{1/2}$ compound 1: >145 min. Hhep stability Tin compound 1: >217 min. Compound 1 displayed permeability and solubility properties as follows: Caco-2 permeability: 29.5×10-6 cm/s; kinetic solubility: 119 uM.

Example 28. CRBN-NTAQ1 Dimerization Biochemical Assay

A TR-FRET CRBN-NTAQ1 dimerization assay was developed to further validate the molecular mode-of-action of compound 1.

Expression and purification of NTAQ1: Human wild-type NTAQ1 (Uniprot ID: Q96HA8 isoform 1) with a tandem N-terminal 6×His-AviTag™ sequence followed by a TEV protease cleavage site was subcloned into a pET28a(+) vector and purchased from Twist Biosciences. The plasmid was transformed into BL-21 Rosetta 2 pLysS *Escherichia coli* cells (Novagen) and used to inoculate 100 mL of LB broth (Invitrogen) supplemented with 50 mg/mL kanamycin (Fisher Scientific) and 35 μg/mL chloramphenicol (Sigma Aldrich). The culture was grown to saturation overnight at 37° C. on an orbital shaker. The following morning, 20 mL of overnight culture was used to inoculate 1 L of LB broth. IPTG (Goldbio) was added to a final concentration of 0.6 mM once the $OD_{600}$ of the culture reached a value of 0.6. Protein production was allowed to occur for 3 hr at 37° C. on an orbital shaker. After 3 hours, the culture was centrifuged for 10 min at 4,000×g, and the supernatant was discarded. The resulting cell pellet was resuspended in 10 mL of PBS (Corning) and transferred to a 50 mL conical tube (Thermo Scientific). The tube was centrifuged for 10 min at 4,000×g and the supernatant was removed. The pellet was washed once more with 10 mL of PBS and the cell pellet was flash frozen in liquid nitrogen and stored at −80° C. For purification, the pellet was thawed and resuspended in 10 mL of cold lysis buffer (50 mM Tris, 200 mM NaCl, 20 mM imidazole, 1 mM TCEP, 1 mM PMSF, pH 8.0). The cell resuspension was lysed on ice water via sonication using a Fisherbrand Model 505 Sonic Dismembrator and ⅛$^{th}$ in. microtip probe; pulsing 20 seconds on/30 seconds off for 3 min of total on time. The lysate was cleared by centrifugation in a Beckman Coulter Optima XE-90 Ultracentrifuge in a Type 45 Ti rotor at 30,000×g for 30 min. The supernatant was transferred to a 15 mL conical tube (Thermo Scientific) with 1 mL of Ni-NTA beads (2 mL 50% slurry) washed with lysis buffer without PMSF. The lysate and beads were incubated with end-over-end rotation (batch binding) for 1 hour at 4° C. The sample was subsequently transferred to a 1.5×10 cm glass Econo-Column® from Bio-Rad. The beads were washed with 20 mL of lysis buffer without PMSF. 5×2 mL volumes of elution buffer (50 mM Tris, 200 mM NaCl, 300 mM imidazole, 1 mM TCEP, pH 8.0). $A_{280}$ measurements were made for each fraction to assess total protein content using elution buffer as a blank. All fractions were pooled. 10 mL of lysis buffer (without PMSF) were prepared with 100 mM biotin, 20 mM ATP, and 20 mM $MgCl_2$. This was added to the 10 mL combined elution. 150 mg of BirA enzyme were added and the sample was mixed and incubated overnight at 4° C. The following morning, the sample was concentrated to 5 mL using a 3 kDa MWCO centrifugation filter (Millipore Sigma), and purified via size-exclusion chromatography (SEC) using a HiLoad 16/600 Superdex 75 pg column (Cytiva Lifesciences) on a Bio-Rad NGC Chromatography System. Integrity of pre-TEV cleavage, post-TEV cleavage, and post-SEC samples were analyzed via SDS-PAGE on a 4-20% Mini-PROTEAN TGX Stain-Free gel from Bio-Rad and imaged on a Bio-Rad GelDoc™ XR+ imager. Confirmation of biotinylation was by mass spectrometry performed using the same method as described above.

CRBN-DDB1 purification: Human CRBN and DDB1 were cloned into pAC-derived vectors and recombinant protein complex was co-expressed as Flag-TEV-Spy-CRBN and His6-Spy-DDB1ΔB fusions in *Trichoplusia ni* High-Five insect cells using the baculovirus expression system (Invitrogen). Cells were lysed by sonication in 50 mM Tris-HCl pH 8.0, 200 mM NaCl, 1 mM TCEP, 1 mM PMSF and 1× protease inhibitor cocktail (Sigma). Following ultracentrifugation and filtration, the soluble fraction was incubated with Flag-M2 sepharose for 1 hr at 4° C. and eluted with buffer (50 mM Tris-HCl pH 8.0, 200 mM NaCl, 1 mM TCEP) containing 150 μg/mL 3×-Flag peptide. The complex was further purified via anion exchange chromatography (Poros 50HQ) and size exclusion chromatography in 25 mM HEPES pH 7.4, 200 mM NaCl and 1 mM TCEP. Fractions containing the purified CRBN-DDB1 complex were concentrated using ultrafiltration (Millipore), flash frozen in liquid nitrogen, and stored at −80° C.

SpyCatcher S50C mutant purification: Spycatcher containing a Ser50Cys mutation was obtained as synthetic dsDNA fragment from IDT (Integrated DNA technologies) and subcloned as His6-TEV fusion protein in a pET-Duet derived vector. SpyCatcher S50C was expressed in BL21 (DE3) *E. coli*. The bacteria were lysed by sonication in buffer containing 50 mM Tris-HCl pH 8.0, 200 mM NaCl, 1 mM TCEP, 1 mM PMSF and 10 mM imidazole. Following ultracentrifugation and filtration, the soluble fraction was passed over Ni Sepharose 6 Fast Flow resin (GE Healthcare) and eluted with buffer containing 50 mM Tris-HCl pH 8.0, 200 mM NaCl, 1 mM TCEP and 200 mM imidazole. The affinity-purified protein was subjected to size exclusion chromatography in 25 mM HEPES pH 7.4, 200 mM NaCl and 1 mM TCEP, concentrated, flash frozen in liquid nitrogen, and stored at −80° C.

Labelling of SpyCatcher with Alexa Fluor 647-C2-maleimide: Purified SpyCatcher$_{S50C}$ protein was incubated with DTT (8 mM) at 4° C. for 1 hr. DTT was removed using a S200 16/600 size exclusion column in a buffer containing 25 mM HEPES pH 7.4, 200 mM NaCl and 1 mM TCEP. Alexa Fluor 647-C2-maleimide (Thermo Fisher) was dissolved in 100/6 DMSO and added to SpyCatcher$_{S550C}$ to achieve 2.5 molar excess of Alexa Fluor 647-C2-maleimide. Labelling was performed at rt for 3 hr before moving to 4° C. overnight. Alexa Fluor 647-labelled Spycatcher$_{S50C}$ was purified on a S200 16/600 size exclusion column in a buffer containing 25 mM HEPES pH 7.4, 200 mM NaCl and 1 mM TCEP, concentrated by ultrafiltration (Millipore), flash frozen in liquid nitrogen, and stored at −80° C.

Alexa Fluor 647-C2-SpyCatcher labelling of CRBN-DDB1ΔB: Spy-tagged CRBN-DDB1 was incubated overnight at 4° C. with Alexa Fluor 647-C2-labelled SpyCatcher$_{S50C}$ protein at 1:1.2 molar ratio of CRBN-DDB1 to SpyCatcher$_{S50C}$. The protein was concentrated and purified using a S200 16/600 size exclusion column in a buffer containing 25 mM HEPES pH 7.4, 200 mM NaCl and 1 mM TCEP. Collected fractions corresponding to the labeled protein were pooled, concentrated by ultrafiltration (Millipore), flash frozen in liquid nitrogen, and stored at −80° C.

TR-FRET dimerization assay: An assay mix containing 100 nM CRBN-DDB1ΔB-SpyCatcher$_{S50C}$-Alexa Fluor 647, 200 nM biotinylated strep-avi-NTAQ1, and 2 nM europium-coupled streptavidin (Invitrogen) in a buffer composed of 50 mM Tris pH 7.5, 200 mM NaCl, 1 mM TCEP, and 0.1% Pluronic F-68 solution (Sigma) was dispensed into a 384-well microplate (Corning, 4514). Compounds were dispensed into the microplate containing assay mix using the D300e Digital Dispenser (HP) normalized to 1% DMSO. The reactions were incubated at room temperature and TR-FRET measurements were conducted at the timepoints indicated in FIG. 5 (0.5 hr, 1 hr, 4 hr). After excitation of europium fluorescence at 337 nm, emission at 665 nm (europium) and 620 nm (Alexa Fluor 647) were recorded with a 70 μs delay over 600 μs to reduce background fluorescence, and the reaction was followed over 5×120 s cycles of each data point using a PHERAstar FS microplate reader (BMG Labtech). The TR-FRET signal was calculated as the average 665/620 nm ratio over 5 cycles for each data point. Data were calculated as an average of 2 technical replicates per concentration of compound, plotted and fit using nonlinear fit variable slope equation in GraphPad Prism 8.

Figure 5:
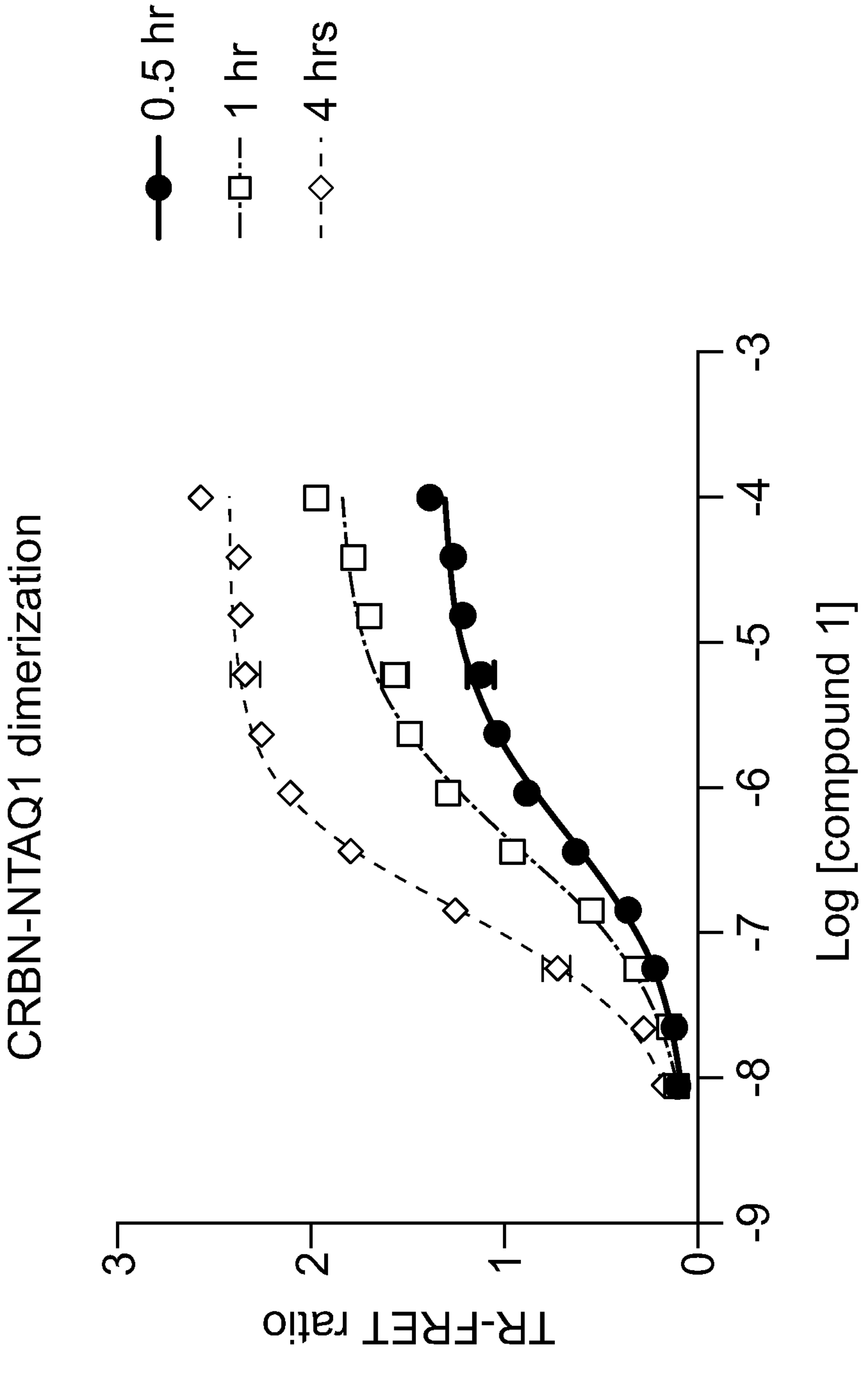
FIG. 5 is a graph of TR-FRET ratio versus Log [compound 1] M that displays the time-dependent dimerization of CRBN and NTAQ1 mediated by compound 1 as measured by TR-FRET.

FIG. 5 shows data that confirms the time-dependent dimerization of CRBN and NTAQ1 mediated by compound 1 as measured by an increase in the TR-FRET ratio.

All patent publications and non-patent publications are indicative of the level of skill of those skilled in the art to which this disclosure pertains. All these publications (including any specific portions thereof that are referenced) are herein incorporated by reference to the same extent as if each individual publication were specifically and individually indicated as being incorporated by reference.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

What is claimed is:

1. A compound of formula (I):

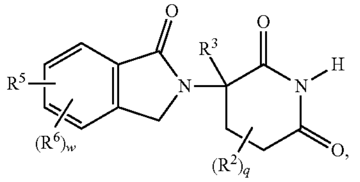

(I)

or a pharmaceutically acceptable salt or stereoisomer thereof, wherein:

each $R^2$ is independently $C_1$-$C_3$ alkyl;

$R^3$ is H or $C_1$-$C_3$ alkyl;

$R^5$ is —$SO_2$—CH═$CH_2$, —$NHSO_2$—CH═$CH_2$, —$SO_2$-(optionally substituted triazolyl), —$SO_2$-(optionally substituted pyrazolyl), —$SO_2$-(optionally substituted imidazolyl), or —$SO_2$-(optionally substituted pyrimidindionyl);

each $R^6$ is independently halogen, —OH, —N(R')$_2$, $C_1$-$C_6$ alkyl, or $C_1$-$C_6$ alkoxy;

each R' is independently H or $C_1$-$C_6$ alkyl;

q is 0, 1, or 2; and w is 0, 1, 2, or 3.

2. The compound of claim 1, or pharmaceutically acceptable salt or stereoisomer thereof, wherein w is 0 or 1.

3. The compound of claim 1, or pharmaceutically acceptable salt or stereoisomer thereof, wherein q is 0.

4. The compound of claim 1, or pharmaceutically acceptable salt or stereoisomer thereof, wherein $R^3$ is H.

5. The compound of claim 1, or pharmaceutically acceptable salt or stereoisomer thereof, wherein $R^5$ is —$SO_2$-(optionally substituted triazolyl), —$SO_2$-(optionally substituted pyrazolyl), —$SO_2$-(optionally substituted imidazolyl), or —$SO_2$-(optionally substituted pyrimidindionyl).

6. The compound of claim 5, or pharmaceutically acceptable salt or stereoisomer thereof, wherein the optionally substituted triazolyl is optionally substituted 1,2,3-triazol-2-yl, optionally substituted 1,2,3-triazol-1-yl, or optionally substituted 1,2,4-triazol-1-yl.

7. The compound of claim 6, or pharmaceutically acceptable salt or stereoisomer thereof, wherein $R^5$ is —$SO_2$-(2H-1,2,3-triazol-2-yl) or —$SO_2$-(1H-1,2,4-triazol-1-yl).

8. The compound of claim 5, or pharmaceutically acceptable salt or stereoisomer thereof, wherein the optionally substituted pyrazolyl is optionally substituted 1,2-pyrazol-1-yl.

9. The compound of claim 8, or pharmaceutically acceptable salt or stereoisomer thereof, wherein $R^5$ is —$SO_2$-(4-methyl-1H-pyrazol-1-yl), —$SO_2$-(4-fluoro-1H-pyrazol-1-yl), —$SO_2$-(4-(trifluoromethyl)-1H-pyrazol-1-yl), —$SO_2$-(3-(trifluoromethyl)-1H-pyrazol-1-yl), or —$SO_2$-(3-fluoro-1H-pyrazol-1-yl).

10. The compound of claim 5, or pharmaceutically acceptable salt or stereoisomer thereof, wherein optionally substituted imidazolyl is optionally substituted 1,3-imidazol-1-yl.

11. The compound of claim 10, or pharmaceutically acceptable salt or stereoisomer thereof, wherein $R^5$ is —$SO_2$-(4-(trifluoromethyl)-1H-imidazol-1-yl), —$SO_2$-(4-methyl-1H-imidazol-1-yl), or —$SO_2$-(4-fluoro-1H-imidazol-1-yl).

12. The compound of claim 5, or pharmaceutically acceptable salt or stereoisomer thereof, wherein optionally substituted pyrimidindionyl is optionally substituted pyrimidin-2,4-dionyl.

13. The compound of claim 12, or pharmaceutically acceptable salt or stereoisomer thereof, wherein $R^5$ is —$SO_2$-(5-methylpyrimidine-2,4 (1H,3H)-dion-1-yl), —$SO_2$-(5-aminopyrimidine-2,4 (1H,3H)-dion-1-yl), or —$SO_2$-(pyrimidine-2,4 (1H,3H)-dion-1-yl).

14. The compound of claim 1, or pharmaceutically acceptable salt or stereoisomer thereof, wherein $R^6$ is —$CH_3$ or —$NH_2$.

15. The compound of claim 1, or pharmaceutically acceptable salt or stereoisomer thereof, which is:

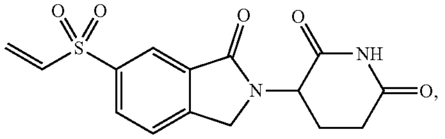

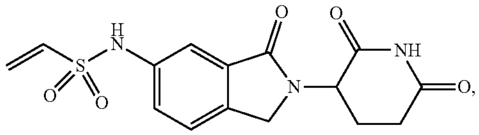

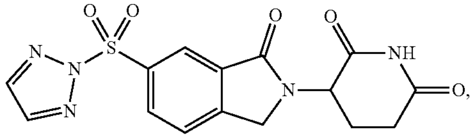

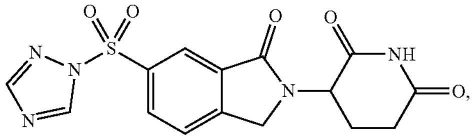

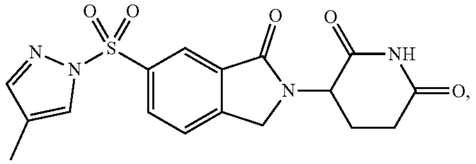

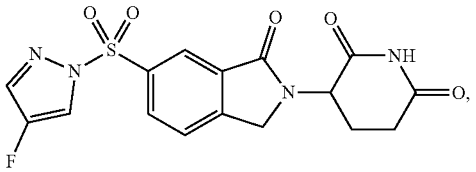

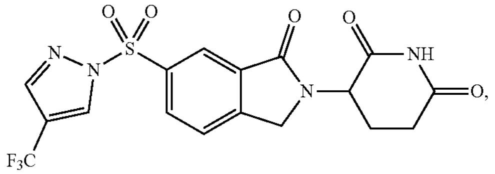

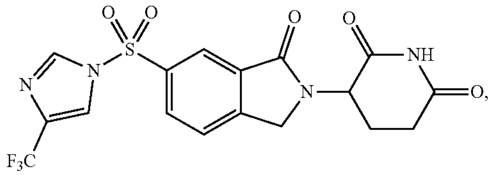

-continued

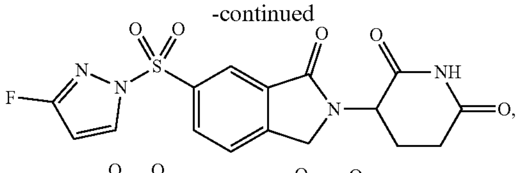

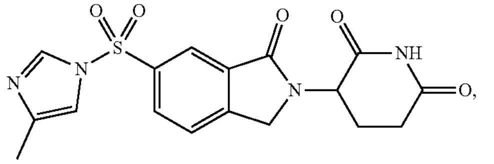

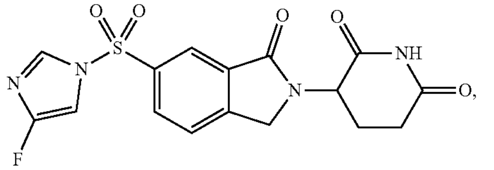

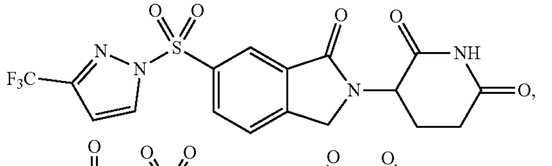

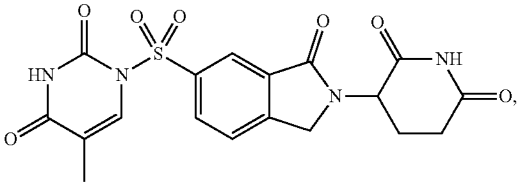

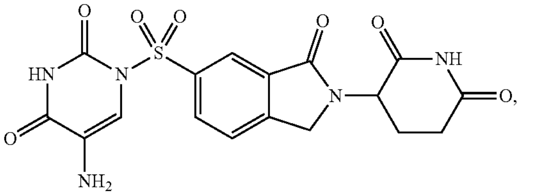

or

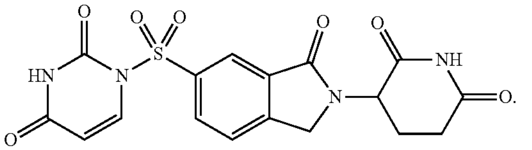

16. A pharmaceutical composition, comprising a therapeutically effective amount of the compound of claim 1, or a pharmaceutically acceptable salt or stereoisomer thereof, and a pharmaceutically acceptable carrier.

17. A method of reducing the level of Protein N-terminal glutamine amidohydrolase (NTAQ1 or WDYHV1) or G1 to S phase transition protein 1 (GSPT1) or 6-phosphofructo-2-kinase/fructose-2,6-biphosphatase 4 (PFKFB4) in a cell, either in vitro or in vivo, comprising contacting the cell with an effective amount of the compound or pharmaceutically acceptable salt or stereoisomer thereof of claim 1.

18. A method of treating a disease or disorder that is characterized by aberrant activity of WDYHV1, GSPT1, or PFKFB4, comprising administering to a subject in need thereof a therapeutically effective amount of the compound or pharmaceutically acceptable salt or stereoisomer thereof of claim 1.

19. The method of claim 18, wherein the disease or disorder is cancer.

20. The method of claim 19, wherein the cancer is gastrointestinal cancer, acute myeloid leukemia, breast cancer, hepatic cancer, pancreatic cancer, glioma, cervical cancer, thyroid cancer, ovarian cancer, lung cancer, bladder cancer or colorectal cancer.

21. A method of covalently engaging cereblon, comprising contacting cereblon with the compound of claim 1, or stereoisomer or pharmaceutically acceptable salt thereof, wherein the compound binds or labels Histidine353 of cereblon.

22. A method of blocking an immunomodulatory drug binding pocket of cereblon, comprising contacting cereblon with the compound of claim 1, or stereoisomer or pharmaceutically acceptable salt thereof, wherein binding of the compound with cereblon inhibits binding between cereblon and any entity that causes cereblon-mediated degradation of a protein target.

23. The compound of claim 1, or pharmaceutically acceptable salt or stereoisomer thereof, wherein $R^5$ is —$SO_2$—CH═$CH_2$ or —$NHSO_2$—CH═$CH_2$.

24. A compound of formula (I):

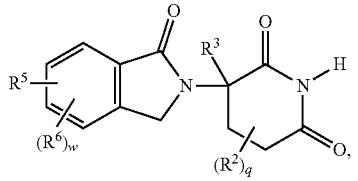

or a pharmaceutically acceptable salt or stereoisomer thereof, wherein:

each $R^2$ is independently $C_1$-$C_3$ alkyl;

$R^3$ is H or $C_1$-$C_3$ alkyl;

$R^5$ is —$SO_2F$ or —$OSO_2F$;

each $R^6$ is independently halogen, OH, —$N(R')_2$, $C_1$-$C_6$ alkyl, or $C_1$-$C_6$ alkoxy;

each R' is independently H or $C_1$-$C_6$ alkyl;

q is 0, 1, or 2; and w is 0, 1, 2, or 3.

25. The compound of claim 24, or pharmaceutically acceptable salt or stereoisomer thereof, which is:

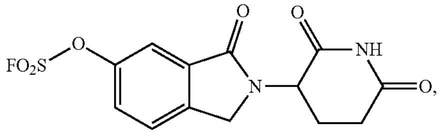

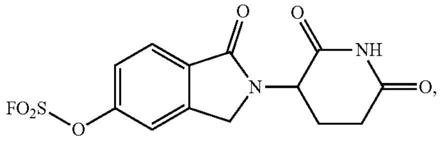

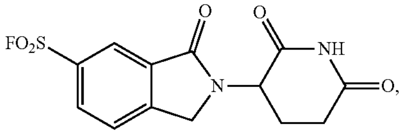

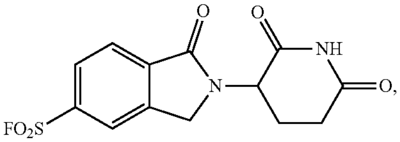

or

-continued

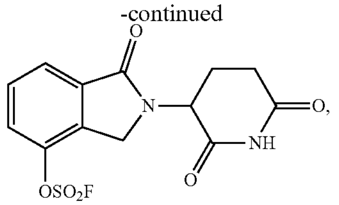

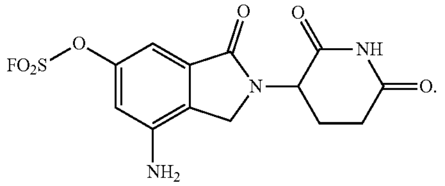

26. A pharmaceutical composition, comprising a therapeutically effective amount of the compound of claim 24, or a pharmaceutically acceptable salt or stereoisomer thereof, and a pharmaceutically acceptable carrier.

27. A method of reducing the level of Protein N-terminal glutamine amidohydrolase (NTAQ1 or WDYHV1) or G1 to S phase transition protein 1 (GSPT1) or 6-phosphofructo-2-kinase/fructose-2,6-biphosphatase 4 (PFKFB4) in a cell, either in vitro or in vivo, comprising contacting the cell with an effective amount of the compound or pharmaceutically acceptable salt or stereoisomer thereof of claim 24.

28. A method of treating a disease or disorder that is characterized by aberrant activity of WDYHV1, GSPT1, or PFKFB4, comprising administering to a subject in need thereof a therapeutically effective amount of the compound or pharmaceutically acceptable salt or stereoisomer thereof of claim 24.

29. The method of claim 28, wherein the disease or disorder is cancer.

30. The method of claim 29, wherein the cancer is gastrointestinal cancer, acute myeloid leukemia, breast cancer, hepatic cancer, pancreatic cancer, glioma, cervical cancer, thyroid cancer, ovarian cancer, lung cancer, bladder cancer or colorectal cancer.

31. A method of covalently engaging cereblon, comprising contacting cereblon with the compound of claim 24, or stereoisomer or pharmaceutically acceptable salt thereof, wherein the compound binds or labels Histidine353 of cereblon.

32. A method of blocking an immunomodulatory drug binding pocket of cereblon, comprising contacting cereblon with the compound of claim 24, or stereoisomer or pharmaceutically acceptable salt thereof, wherein binding of the compound with cereblon inhibits binding between cereblon and any entity that causes cereblon-mediated degradation of a protein target.

* * * * *